(12) United States Patent
Nakamura et al.

(10) Patent No.: US 10,270,998 B2
(45) Date of Patent: Apr. 23, 2019

(54) IMAGING APPARATUS INCLUDING LIGHT SOURCE THAT EMITS PULSED LIGHT BEAM ONTO OBJECT AND LIGHT DETECTOR THAT DETECTS LIGHT RETURNING FROM OBJECT

(71) Applicant: Panasonic Intellectual Property Management Co., Ltd., Osaka (JP)

(72) Inventors: Tatsuya Nakamura, Osaka (JP); Takamasa Ando, Osaka (JP); Teruhiro Shiono, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/834,039

(22) Filed: Dec. 6, 2017

(65) Prior Publication Data
US 2018/0176496 A1    Jun. 21, 2018

(30) Foreign Application Priority Data

Dec. 15, 2016 (JP) .................................. 2016-243290

(51) Int. Cl.
*G01S 3/00* (2006.01)
*H04N 5/33* (2006.01)
(Continued)

(52) U.S. Cl.
CPC .......... *H04N 5/374* (2013.01); *A61B 5/0261* (2013.01); *G01S 3/00* (2013.01); *H04N 5/2353* (2013.01);
(Continued)

(58) Field of Classification Search
CPC .......... A61B 2562/0233; A61B 5/0261; H04N 5/353; H04N 5/374
See application file for complete search history.

(56) References Cited

U.S. PATENT DOCUMENTS 5,305,759 A * 4/1994 Kaneko ................ A61B 5/0059
356/318
2001/0024271 A1    9/2001 Takayanagi et al.
(Continued)

FOREIGN PATENT DOCUMENTS

JP    H04-135551 A    5/1992
JP    4-189349         7/1992
(Continued)

OTHER PUBLICATIONS

Non-Final Office Action issued in U.S. Appl. No. 15/176,165, dated Jul. 16, 2018.

*Primary Examiner* — Amy R Hsu
(74) *Attorney, Agent, or Firm* — McDermott Will & Emery LLP

(57) ABSTRACT

An imaging apparatus includes: a light source that emits a light pulse onto an object, and a light detector that detects a reflected light pulse returning from the object. The light detector detects a first part of the reflected light pulse in a first period, and detects a second part of the reflected light pulse in a second period that starts after the first period. The first period includes at least a part of a rising period, the rising period being a period from start to end of increase of intensity of the reflected light pulse. The second period includes a part of a falling period, starts after start of the falling period and does not include the start of the falling period, the falling period being a period from start to end of decrease of the intensity.

20 Claims, 12 Drawing Sheets

(51) Int. Cl.
  *A61B 5/026* (2006.01)
  *H04N 5/235* (2006.01)
  *H04N 5/353* (2011.01)
  *H04N 5/374* (2011.01)
(52) U.S. Cl.
  CPC ............. *H04N 5/2354* (2013.01); *H04N 5/33* (2013.01); *H04N 5/353* (2013.01); *A61B 2562/0233* (2013.01)

(56) References Cited

U.S. PATENT DOCUMENTS

| | | | |
|---|---|---|---|
| 2004/0215082 A1 | 10/2004 | Chance | |
| 2005/0219545 A1 | 10/2005 | Chan et al. | |
| 2006/0077395 A1* | 4/2006 | Chan | G01B 11/2441 356/497 |
| 2006/0278240 A1 | 12/2006 | Spillman et al. | |
| 2008/0239412 A1* | 10/2008 | Kobayashi | H04N 1/00933 358/475 |
| 2009/0009595 A1* | 1/2009 | Ishiwata | A61B 1/00165 348/68 |
| 2009/0023991 A1* | 1/2009 | Gono | A61B 1/00009 600/109 |
| 2010/0201797 A1* | 8/2010 | Shizukuishi | A61B 1/045 348/68 |
| 2011/0172509 A1 | 7/2011 | Chance | |
| 2011/0230738 A1* | 9/2011 | Chance | A61B 5/0059 600/310 |
| 2015/0173618 A1* | 6/2015 | Kusukame | A61B 5/0064 600/473 |
| 2017/0055845 A1* | 3/2017 | Mirov | A61B 5/0205 |
| 2018/0092602 A1* | 4/2018 | Hall | A61B 5/6891 |

FOREIGN PATENT DOCUMENTS

| | | |
|---|---|---|
| JP | 6-022968 | 2/1994 |
| JP | H11-164826 A | 6/1999 |
| JP | 2003-010189 A | 1/2003 |
| JP | 2003-534030 A | 11/2003 |
| JP | 2005-283472 A | 10/2005 |
| JP | 2006-112864 A | 4/2006 |
| JP | 2006-314557 A | 11/2006 |
| JP | 2007-260123 | 10/2007 |
| JP | 2010-194291 A | 9/2010 |
| JP | 2010-232477 A | 10/2010 |
| JP | 2011-013138 A | 1/2011 |
| JP | 2012-125370 | 7/2012 |
| JP | 2013-224838 | 10/2013 |
| JP | 2015-134157 | 7/2015 |
| WO | 2001/054393 A2 | 7/2001 |

* cited by examiner

IMAGING APPARATUS INCLUDING LIGHT SOURCE THAT EMITS PULSED LIGHT BEAM ONTO OBJECT AND LIGHT DETECTOR THAT DETECTS LIGHT RETURNING FROM OBJECT

RELATED APPLICATION

This application claims the benefit of Japanese Application No. 2016-243290, filed on Dec. 15, 2016, the entire disclosure of which Application is incorporated by reference herein.

BACKGROUND

1. Technical Field

The present disclosure relates to an imaging apparatus that acquires information indicating inside of an object.

2. Description of the Related Art

In the fields of biometrics and material analyses, there is used one type of method that irradiates an object with light, and then acquires internal information of the object in a non-contact manner from information of light passing through the object. For example, Japanese Unexamined Patent Application Publication No. 2015-134157 discloses a method of irradiating a human head with light and detecting light diffused in a living body by using an image sensor such as a CMOS or a CCD. In addition, Japanese Unexamined Patent Application Publication No. 4-189349 discloses a time-resolved detection method that is a method of detecting information at different positions in the depth direction with a streak camera.

SUMMARY

In one general aspect, the techniques disclosed here feature an imaging apparatus that includes: a light source that emits a light pulse onto an object, and a light detector that detects a reflected light pulse returning from the object. The light detector detects a first part of the reflected light pulse in a first period, and detects a second part of the reflected light pulse in a second period that starts after the first period. The first period includes at least a part of a rising period, the rising period being a period from start to end of increase of intensity of the reflected light pulse. The second period includes a part of a falling period, starts after start of the falling period and does not include the start of the falling period, the falling period being a period from start to end of decrease of the intensity.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Underlying Knowledge Forming Basis of the Present Disclosure

Underlying knowledge forming basis of the present disclosure is described before description of embodiments of the present disclosure.

The studies by the present inventors revealed that the above-mentioned related art has the following problems.

In the method described in Japanese Unexamined Patent Application Publication No. 2015-134157, most of the components included in the detected light are components of light reflected off a surface of a living body; that is, there are only a few components of light passed through inside of the living body (e.g., a brain). Thus, it is necessary to detect information indicating inside of the living body more effectively and to separate the surface components and the brain components in the detected information. Meanwhile, in a method disclosed in Japanese Patent No. 5658993, only one-dimensional information can be acquired as space information of the object. In addition, since a streak camera and a light source that emits an ultrashort pulsed light beam having a pulse width on the order of hundred femtoseconds to a few picoseconds are used, the cost is very high.

Figure 1:
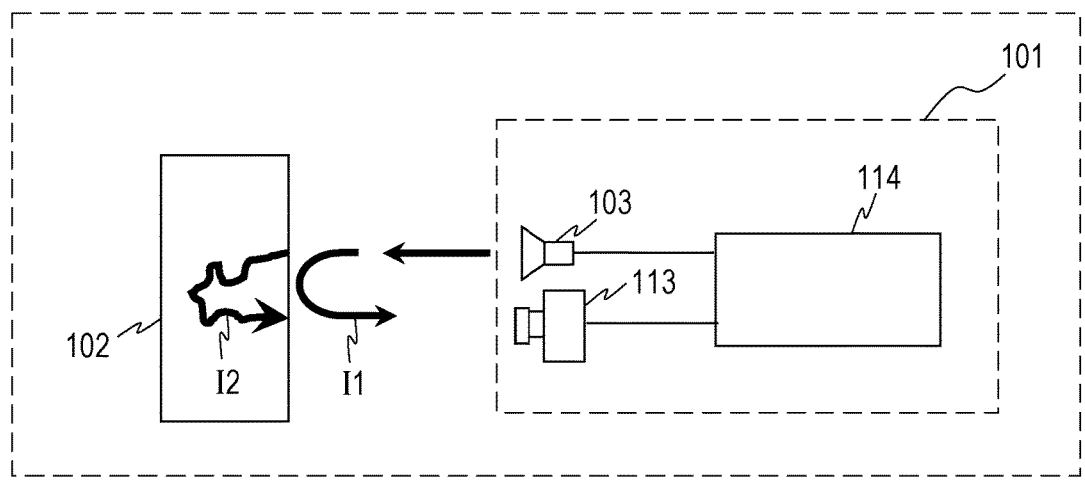
FIG. 1 is a schematic diagram illustrating a schematic configuration of an imaging apparatus.

The present inventors studied an imaging apparatus that is based on a principle different from that of the above-mentioned related art. FIG. 1 is a schematic diagram illustrating a schematic configuration of such an imaging apparatus. The present inventors tried measuring a cerebral blood flow inside a human head that is an object 102 in a non-contact manner using an imaging apparatus 101 as illustrated in FIG. 1. The imaging apparatus 101 includes a first light source 103 which emits a pulsed light beam of a near-infrared region, an image sensor 113 which is a light detector that detects the pulsed light beam emitted by the first light source 103 and then returning from the object 102, and a control circuit 114 which controls the first light source 103 and the image sensor 113.

The first light source 103 is, for example, a laser pulse light source, and repeats emission of a short pulsed light beam having a wavelength of a near-infrared region, in a high-speed pattern determined by the control circuit 114. When a detection target is a living body, the wavelength of light to be emitted by the first light source 103 may be set at, for example, about 650 nm or more but not more than about 950 nm. This wavelength range falls within a wavelength range from red to near-infrared rays, and an absorption factor thereof is low in a living body. Thus, this wavelength range is suitable for a use of acquiring information indicating inside of a living body. In the present specification, a term "light" may be used not only for visible light but also for infrared rays, and the infrared rays may be referred to as "infrared light."

The image sensor 113 has, for example, a high time resolution that allows control of accumulation and discharge of signals in a timescale of picosecond to nanosecond. The control circuit 114 controls a light emission timing of the first light source 103 and an exposure timing of each of the pixels of the image sensor 113.

When the object 102 (e.g., the forehead of a person) is irradiated with light, a surface reflection component I1, which is strong light reflected off the outermost surface of the object 102, first arrives at the image sensor 113. Subsequently, an inside dispersion component I2, which is weak light returning after being dispersed inside the object 102, arrives at the image sensor 113 later than the surface reflection component I1. Information indicating a skin blood flow is mainly reflected on an early part of the inside dispersion component I2 while information indicating a cerebral blood flow is mainly reflected on a late part of the inside dispersion component I2; however, information indicating a skin blood flow and information indicating a cerebral blood flow are mixed at a specific ratio at a certain time in any temporal part of the inside dispersion component I2. Thus, it is necessary to separate the skin blood flow component and the cerebral blood flow component. To deal with this, the present inventors tried detecting the inside dispersion component I2, which is the light dispersed inside the object 102, by using the time-resolved detection method, and to separate the skin blood flow component and the cerebral blood flow component of a living body in the inside dispersion component I2 by using image computation.

Figure 2:
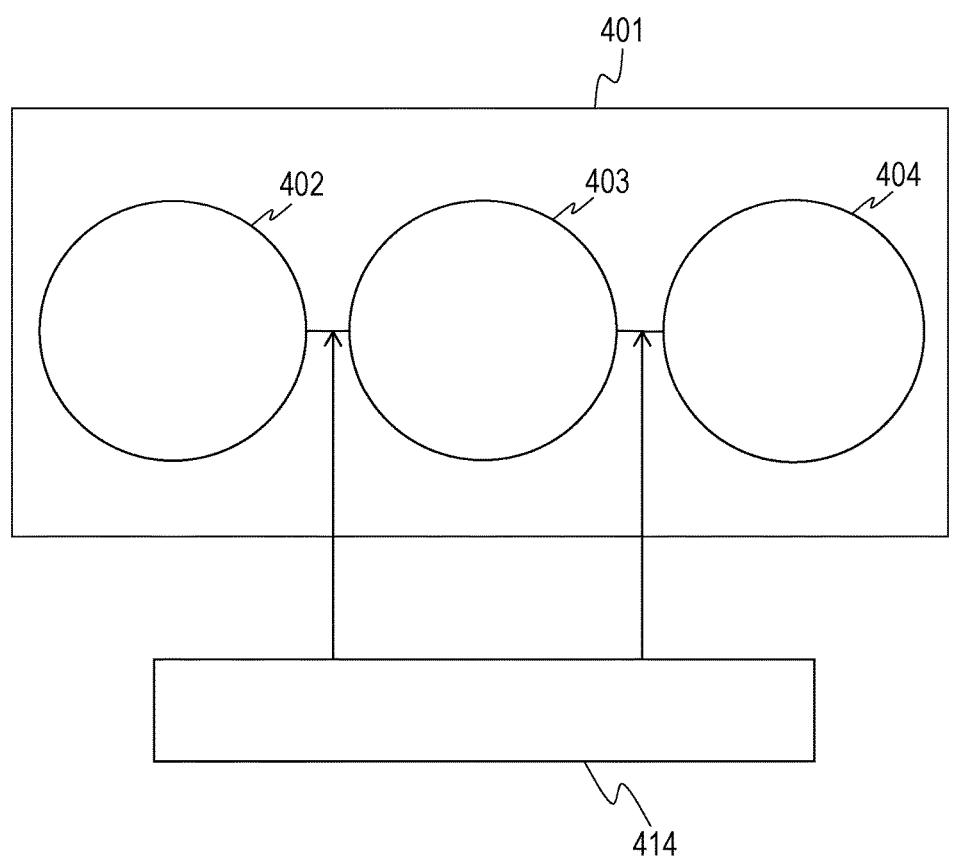
FIG. 2 is a diagram illustrating in a simple manner a configuration of one of pixels in an image sensor.
Figure 3:
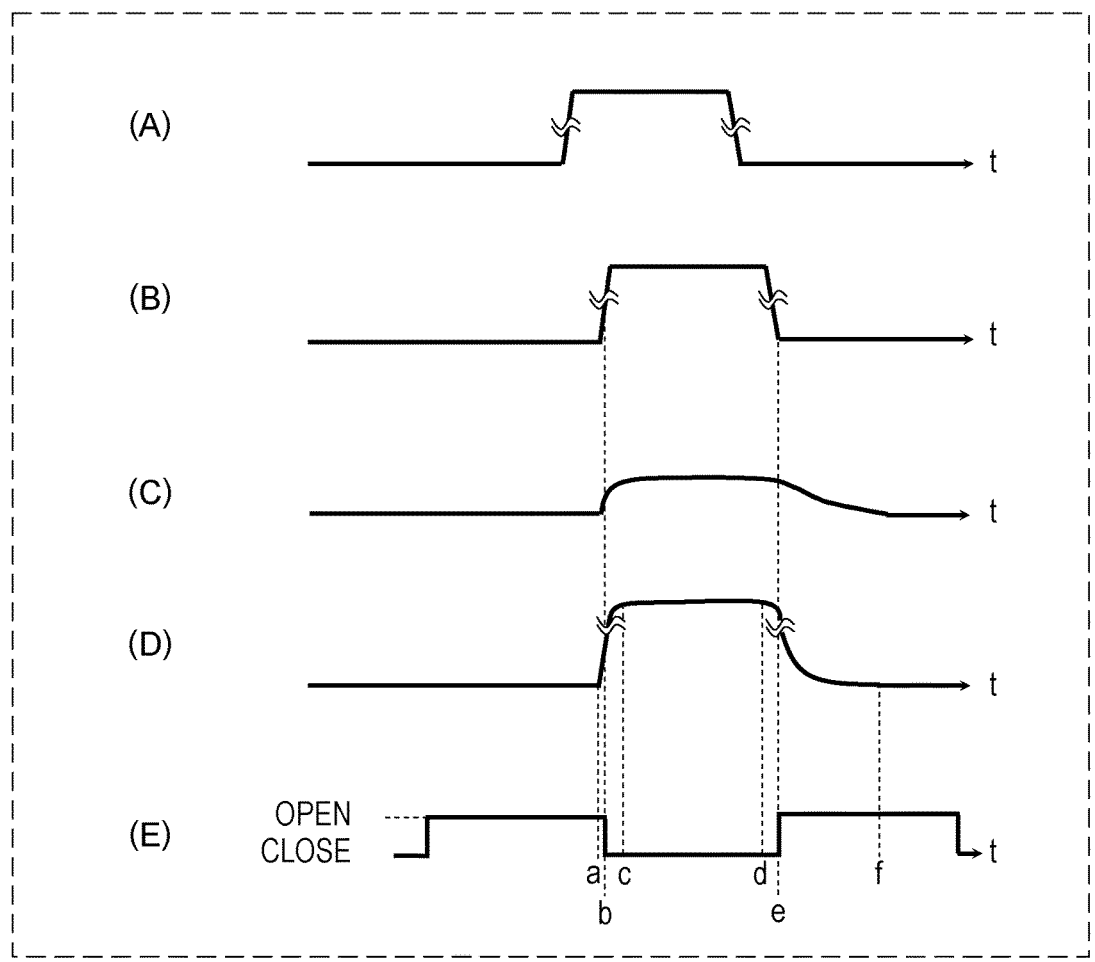
FIG. 3 is a diagram illustrating a relationship between a timing when light is emitted by a light source, a timing when light from an object enters an image sensor, and a timing of an electronic shutter.

Referring to FIGS. 2 and 3, an example of a method of detecting the surface reflection component I1 and the inside dispersion component I2 in the object 102 while separating them is described below.

FIG. 2 is a diagram illustrating in a simple manner a configuration of one of pixels 401 in the image sensor 113. The image sensor 113 has pixels that are two-dimensionally arranged on an imaging plane, and a control circuit 414 that controls a timing of each of accumulation and discharge of the signal charge of each pixel. The control circuit 414 operates based on a command from the control circuit 114.

Each pixel 401 of the image sensor 113 includes a photodiode 403, which is a photoelectric converter, a floating diffusion layer 404, which is an accumulator that accumulates the signal charge, and a drain 402, which discharges the signal charge.

When light (a photon) enters each pixel 401 as a result of light emission of one pulse, the incident light is converted by the photodiode 403 into signal electrons as the signal charge. The signal electrons resulting from the conversion are discharged to the drain 402, or distributed to the floating diffusion layer 404 that accumulates the signal charge, in accordance with a control signal inputted from the control circuit 414. This control performed by the control circuit 414 functions as the electronic shutter.

FIG. 3 is a diagram illustrating a relationship between a timing when a pulsed light beam is emitted by the first light source 103, a timing when light from the object 102 enters the image sensor 113, and a timing of the electronic shutter. In FIG. 3, a signal A indicates a waveform of a pulsed light beam emitted by the first light source 103. A signal B indicates a waveform of the surface reflection component I1, which is light returning after being reflected off a surface of the object 102. A signal C indicates a waveform of the inside dispersion component I2, which is light returning after being dispersed inside a living body. A signal D indicates a waveform that is a combination of the surface reflection component I1 and the inside dispersion component I2. The signal D corresponds to a waveform of the reflected pulsed light beam that is detected by the image sensor 113. A signal E indicates a timing of each of OPEN and CLOSE of the electronic shutter. A horizontal axis represents time, and a vertical axis represents light intensity in the signals A to D, while representing a state of OPEN or CLOSE of the electronic shutter in the signal E. Here, "CLOSE" refers to a state that the signal charge is discharged to the drain 402. Further, "OPEN" refers to a state that the signal charge is not discharged to the drain 402. The control circuit 414 can control the accumulation of the signal charge in the floating diffusion layer 404 and the discharge of the signal charge to the drain 402 by, for example, changing potential energy (hereinafter, simply referred to as "potential") of the signal charge in the floating diffusion layer 404 and the drain 402 through adjustment of a voltage.

When the first light source 103 irradiates the object 102 with a pulsed light beam, the surface reflection component I1 and the inside dispersion component I2 are generated, as described above. Since the inside dispersion component I2 is light passing through the object 102, a light path length thereof is longer than that of the surface reflection component I1. In addition, an average light path length of light that reaches a deep part of a living body such as a brain is longer than that of light that passes through only a shallow part of a living body such as skin and a skull. Thus, part of the inside dispersion component I2, the light that reaches a brain arrives at the image sensor 113 later than the light that passes through only skin. The waveform of the signal D, which corresponds to the waveform of the reflected pulsed light beam detected by the image sensor 113, has a rising period that is a period from the start of increase of intensity of the signal D (at a time a in FIG. 3) to the end thereof (at a time c in FIG. 3), as well as a falling period that is a period from the start of decrease of the intensity of the signal D (at a time d in FIG. 3) to the end thereof (at a time f in FIG. 3). The control circuit 414 causes the electronic shutter of the image sensor 113 to be OPEN before emitting a pulsed light beam and causes the electronic shutter to be CLOSE in middle of the rising period of the waveform of the signal D (at a time b in FIG. 3). This allows the signal charge due to the component with a short light path length that passes through the shallow part of a living body such as, mainly, skin and a skull to be accumulated in the floating diffusion layer 404 in a first period (from the time a to the time b in FIG. 3), which includes at least part of the rising period of the waveform of the signal D. Thereafter, the CLOSE state of the electronic shutter of the image sensor 113 is maintained. Once the surface reflection component I1 ends entering the image sensor 113 (at a time e in FIG. 3), the control circuit 414 causes the electronic shutter to be OPEN. The time e corresponds to a time after the start of the falling period of the signal D. This allows the signal charge resulted from the component with a long light path length that passes through the deep part of a living body such as, mainly, a brain to be accumulated in the floating diffusion layer 404 in a second period (from the time e to the time f in FIG. 3), which is after the start of the falling period of the signal D while including at least part of that falling period. Thereafter, the control circuit 414 causes the electronic shutter to be CLOSE again. After a lapse of a predetermined time following the time when the electronic shutter is caused to be CLOSE, the control circuit 114 starts pulsed-light emission again. Afterward, the operation described above is repeated multiple times (e.g., from about hundred times to about tens of thousands of times). In the meantime, an image of one frame is generated based on the signal charge accumulated in the floating diffusion layer 404.

In this device, when the electronic shutter is CLOSE (i.e., the drain discharge is active), the signal charge is discharged to the drain 402. On the other hand, when the electronic shutter is OPEN (i.e., the drain discharge is inactive), the signal charge is accumulated in the floating diffusion layer 404. The potential of the signal charge in the photodiode 403, the floating diffusion layer 404, and the drain 402 of each of the pixels is designed to implement the above-described operation.

Controlling the electronic shutter in this way to detect a rising component, which is a component in the rising period, and a falling component, which is a component in the falling period, from the pulsed light beam returning from a living body makes it possible to acquire information indicating a skin blood flow and information indicating a cerebral blood flow. In this case, in consideration of a dynamic range of the image sensor, it is preferable to not saturate signal amounts of the detected rising component and falling component. Since the light that enters a living body and returns after reaching a brain passes through skin, the falling component particularly includes not only information indicating a cerebral blood flow but also much information indicating a skin blood flow. As described later, the present inventors tried to separate skin blood flow information and cerebral blood flow information by imaging the rising and falling components detected by the image sensor and then computing the image.

As an imaging apparatus that operates similarly to the above electronic shutter drive, there is the time-of-flight (TOF) method for measuring a distance to an object. In the TOF method, the object is irradiated with a pulsed light beam to detect a first part and a second part of a reflected pulsed light beam. In the TOF method, in order to detect a large amount of light, the reflected pulsed light beam is detected such that both the first and second parts include a part having the maximum intensity of the waveform of the reflected pulsed light beam.

In contrast, in the imaging apparatus according to one aspect of the present disclosure, since the second period is a period after the start of the falling period of the waveform of a reflected pulsed light beam and does not include the start of the falling period, the second period does not include a part having the maximum intensity of the reflected pulsed light beam.

The present disclosure includes aspects described in the following items, for example.

Item 1

An imaging apparatus according to Item 1 includes:
a light source that emits a light pulse onto an object, and
a light detector that detects a reflected light pulse returning from the object.
The light detector detects a first part of the reflected light pulse in a first period, and detects a second part of the reflected light pulse in a second period that starts after the first period.
The first period includes at least a part of a rising period, the rising period being a period from start to end of increase of intensity of the reflected light pulse.
The second period includes a part of a falling period, starts after start of the falling period and does not include the start of the falling period, the falling period being a period from start to end of decrease of the intensity.

Item 2

In the imaging apparatus according to Item 1,
the light detector may be an image sensor that includes pixels, each of the pixels including
a photoelectric converter that converts light returning from the object into a signal charges, and
an accumulator that accumulates the signal charges, and
the image sensor may accumulate the signal charges by the accumulator in the first period and may accumulate the signal charges by the accumulator in the second period.

Item 3

In the imaging apparatus according to Item 2,
the image sensor may not accumulate the signal charges by the accumulator in a third period that is between the rising period and the falling period.

Item 4

In the imaging apparatus according to Item 2 or 3,
in each of frame periods, the image sensor may acquire an image of the object of one frame based on the signal charges accumulated in the accumulator, the frame periods include a first frame period and a second frame period that is different from the first frame period, and the first period and the second period may be included in the first frame period and the second frame period respectively.

Item 5

In the imaging apparatus according to any one of Items 2 to 4, each of the pixels may include a first accumulator and a second accumulator, and the image sensor may accumulate the signal charges by the first accumulator in the first period and may accumulate the signal charges by the second accumulator in the second period.

Item 6

In the imaging apparatus according to Item 5, in each of frame periods, the image sensor may acquire an image of the object of one frame based on the signal charges accumulated in the accumulators, and the first period and the second period may be included in the same frame period in the frame periods.

Item 7

In the imaging apparatus according to Item 1, the first period and second period may be discontinuous.

Item 8

In the imaging apparatus according to Item 1, the first period and the second period may be shorter than a pulse width of the light pulse.

Item 9

In the imaging apparatus according to Item 2, the light source may emit a first light pulse and a second light pulse onto the object, each of the first light pulse and the second light pulse being the light pulse, the light detector may detect a first reflected light pulse and a second reflected light pulse returning from the object, each of the first reflected light pulse and the second reflected light pulse being the reflected light pulse, and the image sensor may accumulate the signal charges by the accumulator in the first period of the first reflected light pulse and may accumulate the signal charges by the accumulator in the second period of the second reflected light pulse.

Item 10

In the imaging apparatus according to any one of Items 2 to 6, the light source may emit a plurality of light pulses onto the object, each of the plurality of light pulses being the light pulse, the light detector may detect a plurality of reflected light pulses returning from the object, each of the plurality of reflected light pulses being the reflected light pulse, the image sensor may accumulate the signal charges by the accumulator in first periods and may accumulate the signal charges by the accumulator in second periods, each of the first periods may be the first period while each of the second periods is the second period, and the number of the first periods may be smaller than the number of the second periods.

Item 11

In the imaging apparatus according to Item 1, the light source may emit a first light pulse and a second light pulse onto the object, each of the first light pulse and the second light pulse being the light pulse, and the light detector may detect a first reflected light pulse in the first period of the first reflected light pulse and a second reflected light pulse in the second period of the second reflected light pulse, each of the first reflected light pulse and the second reflected light pulse being the reflected light pulse.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or an LSI. The LSI or IC can be integrated into one chip, or also can be a combination of plural chips. For example, functional blocks other than a memory may be integrated into one chip. The name used here is LSI or IC, but it may also be called system LSI, VLSI (very large scale integration), or ULSI (ultra large scale integration) depending on the degree of integration. A Field Programmable Gate Array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a ROM, an optical disk or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

Embodiment 1

The imaging apparatus of this embodiment uses a light dispersion body, such as a living body, as the target object. To be more specific, the imaging apparatus of this embodiment detects a distribution of amounts of change in blood flows of surface skin and a brain of a subject to be observed and detects a temporal change therein. This makes it possible to generate a two-dimensional image that is a still image or moving image indicating this distribution. For example, it is possible to estimate brain activity (e.g., concentration or feelings) of the subject, by using information indicating this image. The imaging apparatus of this embodiment can detect such biometric information in a non-contact manner, and thus can address inconvenience accompanying the detection. This makes it possible to greatly enhance detection accuracy of the cerebral blood flow information, as compared with existing techniques. A configuration and operation of the imaging apparatus of this embodiment that can perform such highly accurate detection are described below.

1. Configuration

Figure 4:
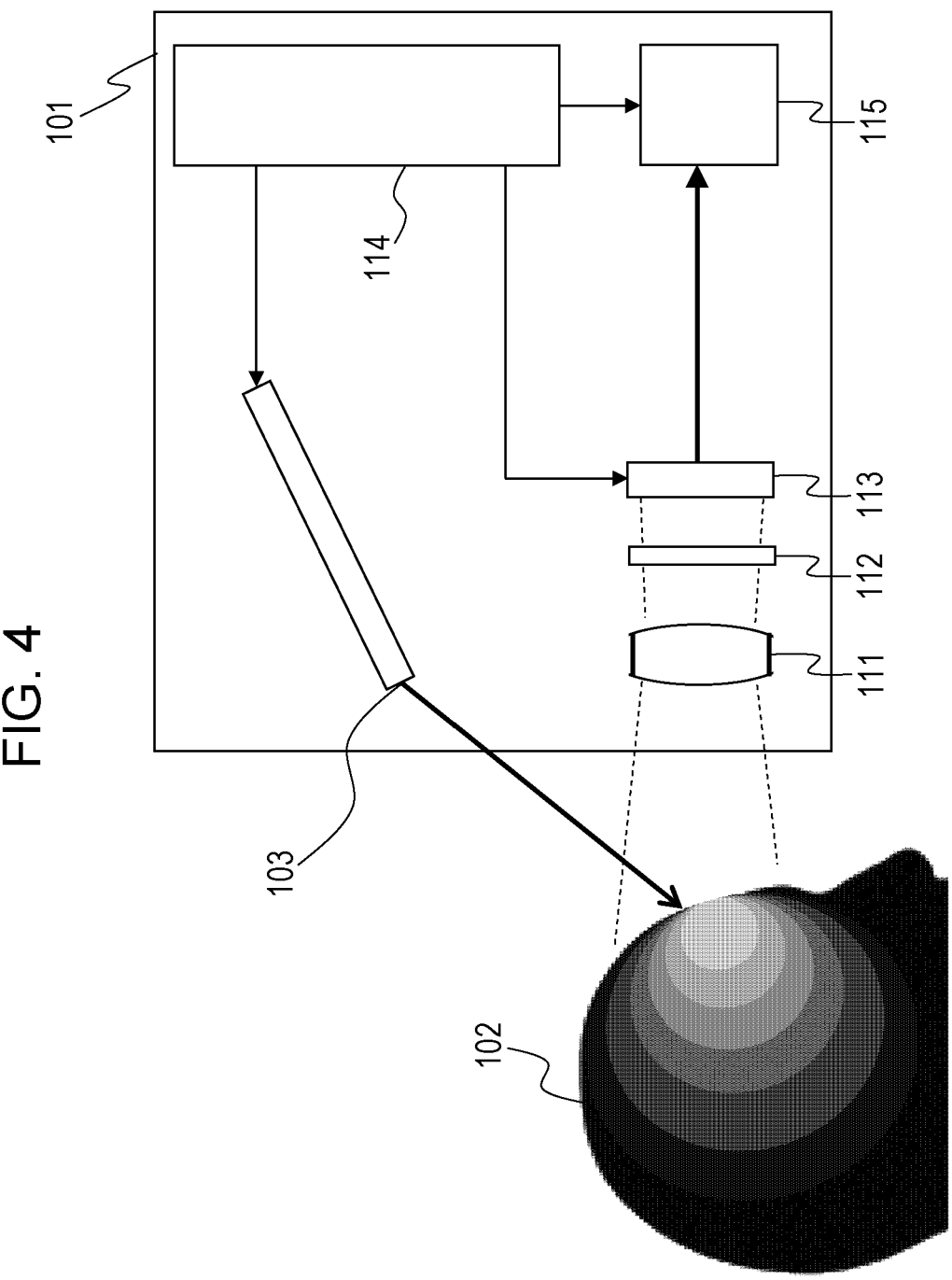
FIG. 4 is a diagram schematically illustrating a configuration of an imaging apparatus according to Embodiment 1 of the present disclosure.

FIG. 4 is a diagram schematically illustrating a configuration of the imaging apparatus 101 in this embodiment. FIG. 4 illustrates not only the imaging apparatus 101, but also the object 102 (a human head), which is serving as a detection target.

The imaging apparatus 101 includes the first light source 103, the image sensor 113, which is a light detector, a band-pass filter 112, an optical system 111, the control circuit 114, and a signal processing circuit 115. The first light source 103 emits a pulsed light beam toward a point where the object 102 is located. In this embodiment, the first light source 103 is a laser light source that emits a narrow-band pulsed light beam having a center wavelength of 750 nm. The image sensor 113 is disposed on an image formation plane of the optical system 111, and detects light reflected from the object 102. The optical system 111 is disposed between the object 102 and the image sensor 113, and may include one or more lenses. The optical system 111 condenses light from the object 102, thereby forming an image on an imaging plane of the image sensor 113. The band-pass filter 112 is disposed between the optical system 111 and the image sensor 113, and mainly allows only light having a wavelength corresponding to a wavelength of a ray from the first light source 103 to pass therethrough.

The control circuit 114 is connected to the first light source 103 and the image sensor 113, and controls operation of these components. To be more specific, the control circuit 114 performs control, by synchronizing a light emission timing of the first light source 103 with a timing of signal accumulation and signal discharge of each pixel of the image sensor 113. This makes it possible to detect information indicating a scalp blood flow and a cerebral blood flow in a living body with high accuracy. The signal processing circuit 115 is connected to the image sensor 113. Based on the information, which is an electric signal outputted from the image sensor 113, the signal processing circuit 115 generates image data (e.g., data of a two-dimensional moving image) and outputs the generated image data. The generated image data is sent to, for example, a display (not illustrated) that can display an image illustrating a state of a cerebral blood flow. The signal processing circuit 115 may be provided in an apparatus provided outside the imaging apparatus 101. For example, an external computer connected to the imaging apparatus 101 by wire or wirelessly may include the signal processing circuit 115. According to such an aspect, it is not necessary for the imaging apparatus 101 to perform computation with a high calculation load, and thus, it is possible to configure the imaging apparatus 101 at low cost. The imaging apparatus 101 can include other components not illustrated in FIG. 4. For example, the imaging apparatus 101 may include an optical system such as a mirror that changes the traveling direction of light from the first light source 103, a communication circuit that performs wireless communication, and the like.

It is not necessary for components illustrated in FIG. 4 to be disposed inside the same housing. For example, the imaging apparatus 101 can be implemented by combining an information terminal such as a smartphone or a tablet computer with another device connected to this information terminal. Such another device can include the first light source 103, the image sensor 113, the band-pass filter 112, and the optical system 111. It is possible to cause a processor (a CPU, a GPU, and the like) of the information terminal to function as the control circuit 114 and the signal processing circuit 115 by installing specific software onto the information terminal.

Each of the components is described in more detail below.

1-1. First Light Source 103

The first light source 103 in this embodiment is a laser pulse light source that emits a narrow-band pulsed light beam having a center wavelength of 750 nm. As described later, the first light source 103 emits a pulsed light beam repeatedly in a predetermined pattern determined by the control circuit 114. The pulsed light beam emitted by the first light source 103 can be, for example, light having a rectangular waveform in which a rising time, which is a time from the start of a rise to completion of the rise, as well as a falling time, which is a time from the start of a fall to completion of the fall, are close to zero. The first light source 103 can be a light source such as a laser diode (LD) in which a rising part and a falling part of a pulsed light beam is nearly perpendicular to a time axis (i.e., have time response characteristics of rapid progress type). Any type of light source that emits a pulsed light beam can be used for the first light source 103. Examples of this light source include a semiconductor laser, a solid-state laser, and a fiber laser.

In the imaging apparatus 101 of this embodiment, the object 102 is a human body, and thus the first light source 103 reflecting consideration of an influence on retina can be used. For example, when a laser light source is used, a light source satisfying Class 1 of laser safety standards devised in each country can be used. When Class 1 is satisfied, the object 102 is irradiated with light of low light intensity to the extent that accessible emission limit (AEL) is below 1 mW. Even if the first light source 103 itself does not satisfy Class 1, the first light source 103 is acceptable if the first light source 103 satisfies Class 1 when combined with another optical element. For example, Class 1 of the laser safety standard may be satisfied by diffusing or attenuating light, by providing an element such as a diffuser or an ND filter between the first light source 103 and the object 102.

The wavelength of light emitted by the first light source 103 is not limited to 750 nm. For example, light having any wavelength within a wavelength range of 650 nm to 950 nm (red light or near-infrared light) can be used. This wavelength region is called "the biological window," which has a property of being comparatively less likely to be absorbed into moisture and skin of a living body. In a case of using a living body as a detection target, using light within the above wavelength region makes it possible to enhance detection sensitivity. In a case of detecting a change in blood flows of skin and a brain of the object 102 like this embodiment, light that is used for this case is believed to be absorbed mainly into oxygenated hemoglobin and deoxygenated hemoglobin, while a degree of the absorption of light with respect to each wavelength is different. When there is a change in a blood flow, it is considered that concentration of oxygenated hemoglobin and deoxygenated hemoglobin is changed, and thus the degree of the absorption of light is also changed. As a result, a detected light amount before and after the change in a blood flow is different.

In the present disclosure, the object 102 is not limited to a living body. For example, any of other types of light dispersing bodies such as gas, medicine, and food can be adopted as the object 102. The wavelength region of the light emitted by the first light source 103 is not limited to a wavelength region of near-infrared rays (about 700 nm to about 2500 nm), and may be, for example, a wavelength region of visible light (about 400 nm to about 700 nm) or a wavelength region of ultraviolet rays (about 10 nm to about 400 nm). Mid-infrared rays, far-infrared rays, or electromagnetic waves in a region of radio waves such as terahertz waves or millimeter waves can also be used depending on an intended use.

As described with reference to FIG. 1, the light arriving at the object 102 from the first light source 103 is divided into the surface reflection component I1, which is reflected off a surface of the object 102, and the inside dispersion component I2, which is reflected or dispersed once, or dispersed multiple times, in the object 102. The surface reflection component I1 includes two components: a direct reflection component and a diffuse reflection component. The direct reflection component is a component that is reflected at a reflection angle equal to an incident angle. The diffuse reflection component is a component that is diffused and reflected due to unevenness of the surface. In the present disclosure, the surface reflection component I1 reflected off the surface of the object 102 includes these two components. Meanwhile, the inside dispersion component I2 includes a component that is dispersed and reflected due to internal tissue near the surface. The surface reflection component I1 and the inside dispersion component I2 each changes a traveling direction by reflection or dispersion, and part thereof arrives at the image sensor 113 after passing through the optical system 111 and the band-pass filter 112.

1-2. Optical System 111 and Band-Pass Filter 112

The optical system 111 in this embodiment is intended to effectively form an image with light in the image sensor 113, and may be lenses combined with each other or may be a single lens. Otherwise, the optical system 111 may also be a telecentric optical system. In order to adjust an angle of view of the object, a fish-eye lens, a wide lens, and a zoom lens may be used. In addition, in order to adjust brightness, a pupil may be provided in front, back, or middle of the lens.

Figure 5:
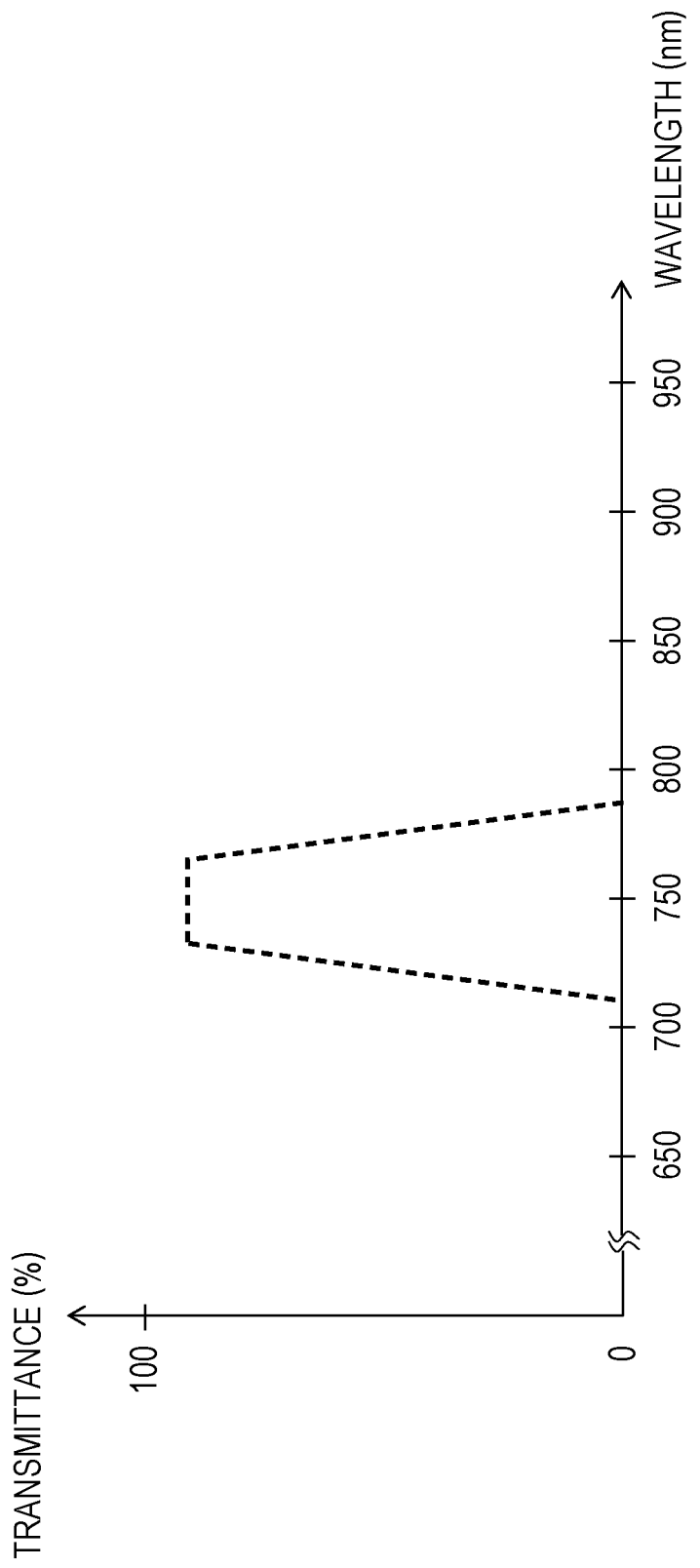
FIG. 5 is a graph illustrating an example of spectral transmittance of a band-pass filter.

The band-pass filter 112 is a filter that mainly allows light of 750 nm. FIG. 5 is a graph illustrating an example of spectral transmittance of the band-pass filter 112. As illustrated in the drawing, the band-pass filter 112 allows narrow-band light having a center wavelength of 750 nm and emitted by the first light source 103, and blocks light of other wavelengths. It is possible to suppress disturbance light (e.g., background light) from entering the image sensor 113, by disposing the band-pass filter 112 described above.

1-3. Image Sensor 113

The image sensor 113 receives light emitted by the first light source 103 and reflected by the object 102. The image sensor 113 has pixels two-dimensionally arranged on an imaging plane, and acquires two-dimensional information indicating the inside of the object 102. The image sensor 113 can be, for example, a CCD image sensor or a CMOS image sensor.

The image sensor 113 has an electronic shutter. The electronic shutter is a circuit that controls a shutter width corresponding to the length of an exposure period in which received light is converted into an effective electric signal and stored once. The circuit also controls time from the end of one exposure period to the start of the next exposure period. In the present specification, a state where exposure is performed by the electronic shutter is expressed as "OPEN," and a state where exposure is stopped by the electronic shutter is expressed as "CLOSE." The image sensor 113 can adjust a time from ending of one exposure period to the start of the next exposure period by the electronic shutter on a timescale of sub-nanosecond (e.g., 30 ps to 1 ns). In this embodiment, unlike a conventional time-of-flight (TOF) camera intended to measure a distance to an object, it is not necessary to make a shutter width larger than a pulse width. To correct brightness of an object, the conventional TOF camera detects all of pulsed light beams emitted by a light source and reflected by the object.

Thus, in the conventional TOF camera, it is necessary to provide a shutter width larger than a pulse width of light. In contrast, in the imaging apparatus 101 of this embodiment, it is not necessary to correct an amount of light from the object, and thus, it is not necessary to provide a shutter width larger than a pulse width. In this embodiment, the shutter width can be, for example, of the order of about 1 ns to about 30 ns. According to the imaging apparatus 101 of this embodiment, it is possible to make the shutter width shorter than that in a conventional apparatus, and thus, it is possible to reduce dark current included in a detection signal.

Assume that the object 102 is, for example, the forehead of a person, and an intended purpose is to detect information indicating a cerebral blood flow or the like. In this case, an attenuation factor of light inside the object 102 is very large. For example, the light can be attenuated to a level of the order of about one millionth. Thus, to detect the inside dispersion component I2, a light amount may be short if the light amount corresponds to irradiation of only one pulse. In this case, the first light source 103 may emit a pulsed light beam multiple times, and the image sensor 113 may accordingly perform exposure with the electronic shutter multiple times. According to such operation, a detection signal is multiplied, which makes it possible to enhance sensitivity.

A configuration of a pixel is the same as that in FIG. 2. FIG. 2 schematically illustrates a configuration of one of the pixels 401, and does not necessarily reflect a real structure. The pixel 401 includes the photodiode 403, which performs photoelectric conversion, the floating diffusion layer 404, which is an accumulator that accumulates the signal charge, and the drain 402, which discharges the signal charge. Functions of the floating diffusion layer 404 and the drain 402 are the same as the functions already described with reference to FIG. 2.

The image sensor 113 includes the control circuit 414 that controls accumulation and discharge of the signal charge in each of the pixels 401, based on a command from the control circuit 114. The control circuit 414 can be a circuit (e.g., a microcontroller unit) having a processor and a memory. In accordance with a control program stored in the memory, the control circuit 414 controls accumulation of the signal charge to the floating diffusion layer 404, and discharge of the signal charge to the drain 402, in response to an instruction from the control circuit 114 externally provided. In this way, the image sensor 113 can perform imaging with a high time resolution, and thus may be referred to as "a time-resolved image sensor."

The light that enters each of the pixels 401 as a result of light emission of one pulse is converted by the photodiode 403 into signal electrons that are the signal charge. The signal electrons resulting from the conversion are discharged to the drain 402, or distributed to the floating diffusion layer 404, in accordance with a control signal inputted from the control circuit 414.

Figure 6:
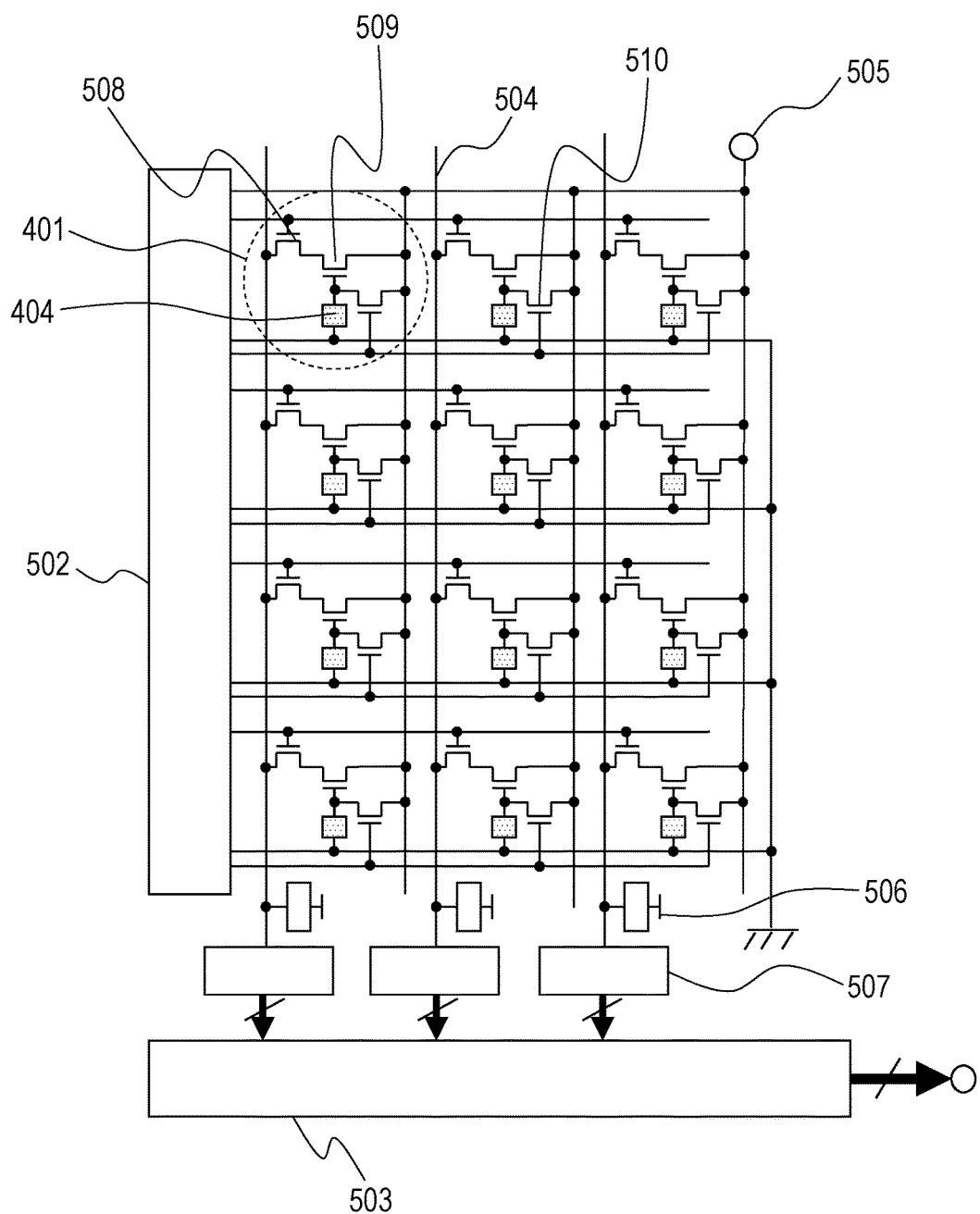
FIG. 6 is a diagram illustrating a schematic configuration of one of pixels in the image sensor.

FIG. 6 is a diagram schematically illustrating an example of a configuration of the image sensor 113. In FIG. 6, an area surrounded by a dashed frame corresponds to one of the pixels 401. The pixel 401 includes the floating diffusion layer 404. A signal accumulated in the floating diffusion layer 404 is handled like a signal of a pixel of a general CMOS image sensor and is outputted from the image sensor 113. In FIG. 6, illustrated are only elements that are related to low-speed reading operation, which is operation of outputting the signal charge in the floating diffusion layer 404 from the image sensor 113 after accumulation of the signal charge into the floating diffusion layer 404 is completed. The drain 402, the photodiode 403, and the control circuit 314 are not directly related to the low-speed reading operation, thereby not being illustrated in FIG. 6.

The pixel 401 includes three signal detection circuits. Each signal detection circuit includes a source follower transistor 509, a row selection transistor 508, and a reset transistor 510. In this example, the reset transistor 510 corresponds to the drain 402 illustrated in FIG. 2. A pulsed signal inputted to a gate of the reset transistor 510 controls discharge of the signal charge. Each transistor is a field-effect transistor formed on a semiconductor substrate, for example; however, it is not limited thereto. As illustrated in the drawing, one of an input terminal and an output terminal of the source follower transistor 509 (typically, a source) and one of an input terminal and an output terminal of the row selection transistor 508 (typically, a drain) are connected. A gate that is a control terminal of the source follower transistor 509 is electrically connected to the photodiode 403, which is not illustrated in FIG. 6. A hole or an electron that is the signal charge generated by the photodiode 403 is accumulated in the floating diffusion layer 404, which is an accumulator provided between the photodiode 403 and the source follower transistor 509.

Once a row selection circuit 502 causes a gate of the row selection transistor 508 to be ON, the signal charge accumulated in the floating diffusion layer 404 is to be read. At this time, in accordance with potential of the signal of the floating diffusion layer 404, current flowing from a source follower power source 505 into the source follower transistor 509 and a source follower load 506 is amplified. An analog signal due to the current read from a perpendicular signal line 504 is converted into digital signal data by an analog-digital (AD) converter circuit 507 connected to each row. The digital signal data is read from each row by a column selection circuit 503 and outputted from the image sensor 113.

After reading from one row is completed, the row selection circuit 502 and the column selection circuit 503 performs reading from the next row, and sequentially read information indicating the signal charge of the floating diffusion layer from all the rows in the same manner. After reading all the signal charge, the control circuit 414 causes the gate of the reset transistor 510 to be ON to reset all the floating diffusion layers. In this way, imaging of one frame is completed. By repeating the high-speed imaging of the frames in the same manner, imaging of a series of frames by the image sensor 113 is completed.

In this embodiment, an example of using the image sensor 113 of CMOS type is described. However, the image sensor 113 may be any of a CCD-type image sensor, a single photon counting element, and an amplification-type image sensor such as an EMCCD, or an ICCD.

1-4. Control Circuit 114 and Signal Processing Circuit 115

The control circuit 114 can be, for example, a combination of a microprocessor and a memory, or an integrated circuit such as a microcontroller including a processor and a memory built therein. The control circuit 114 provides a lighting instruction to the first light source 103, an imaging instruction to the image sensor 113, a computation instruction to the signal processing circuit 115, and the like. Based on an instruction from the control circuit 114, the control circuit 414 in the image sensor 113 controls accumulation and discharge of the signal charge in each of the pixels.

The signal processing circuit 115 is a circuit that processes an image signal outputted from the image sensor 113. The signal processing circuit 115 can be implemented by, for example, a digital signal processor (DSP), a programmable logic device (PLD) such as a field programmable gate array (FPGA), or a combination of a central processing unit (CPU) or a graphic processing unit (GPU) with a computer program. The control circuit 114 and the signal processing circuit 115 may be implemented by one unified circuit.

Based on the signal outputted from the image sensor 113, the signal processing circuit 115 in this embodiment generates moving image data that indicates a temporal change of blood flows of skin and a brain. The signal processing circuit 115 may generate not only the moving image data but also other information. For example, the signal processing circuit 115 may generate biometric information such as a blood flow rate, a blood pressure, and a blood oxygen saturation level in a brain, or heartbeats by being synchronized with another device.

It is known that there is a close relationship between a change in a cerebral blood flow rate or a component in blood flow (e.g., hemoglobin) and a human neural activity. For example, a cerebral blood flow rate or a component in blood flow changes, as the neuronal activity changes in response to a change in human feeling. Thus, it is possible to estimate a psychological condition of a subject, if it is possible to measure biometric information such as a change in a cerebral blood flow rate or a component in blood flow. Examples of the psychological condition of the subject include moods (e.g., pleasantness and unpleasantness), feelings (e.g., ease, anxiety, sadness, and anger), health conditions (e.g., cheerfulness and laziness), and temperature senses (e.g., hotness, coldness, and humidity). The examples of the psychological condition further include conditions deriving from the above examples, such as indexes representing the degrees of brain activities including a level of skill, a learning level, and a degree of concentration. The signal processing circuit 115 may estimate a psychological condition such as a degree of concentration of a subject based on a change such as a change in a cerebral blood flow rate, and then output a signal indicating an estimation result.

2. Operation

Next, operation of the imaging apparatus 101 of this embodiment is described with reference to FIGS. 7A and 7B.

Most of energy of light at the wavelength of 750 nm emitted to the head, which is the object 102, is reflected off the surface of the object 102, as described with reference to FIG. 1. However, small portion of component arrives at a deep part of the object 102 while being dispersed, and then a small amount of energy component being further dispersed arrives again at the surface of the forehead of the head as the inside dispersion component. Part of this light passes through the optical system 111 and the band-pass filter 112, and then arrives at the image sensor 113.

Figure 7A:
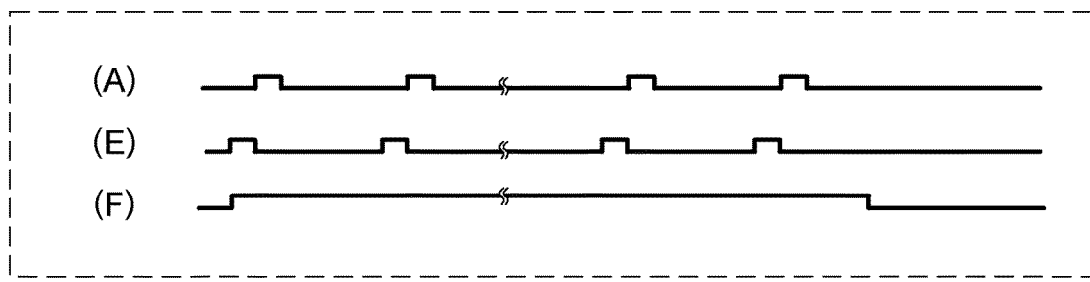
FIG. 7A is a timing diagram illustrating an example of operation of the imaging apparatus in a period of acquiring an image signal of a first frame period in Embodiment 1.

In view of this, as illustrated in FIG. 7A, the control circuit 114 in this embodiment causes the electronic shutter of the image sensor to be OPEN in a first frame period before emission of a pulsed light beam, and maintains the OPEN state of the electronic shutter during a period corresponding to a light emission pulse width. Then, in middle of rising of the reflected light arriving at the image sensor 113, the control circuit 114 causes the electronic shutter to be CLOSE. Afterward, the next pulsed light beam is emitted, and the same operation is performed. Repeating the above-described operation makes it possible to detect light that mainly passes through skin and a skull only.

Figure 7B:
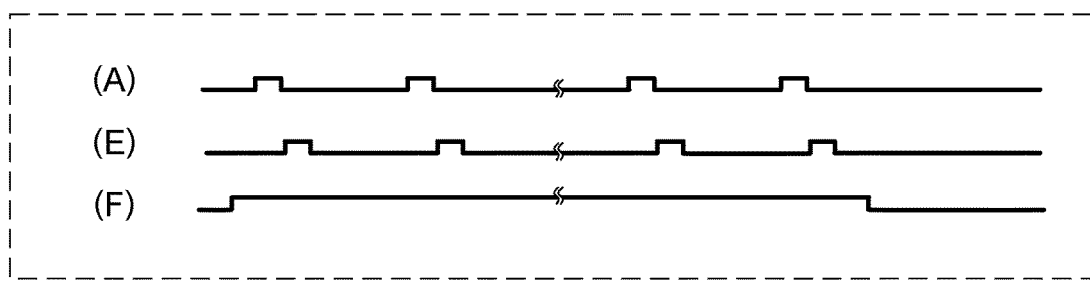
FIG. 7B is a timing diagram illustrating an example of operation of the imaging apparatus in a period of acquiring an image signal of a second frame period in Embodiment 1.

As illustrated in FIG. 7B, in each pixel of the image sensor 113 in a second frame period, the control circuit 114 sets the electronic shutter to CLOSE during incidence of the surface reflection component of the pulsed light beam, and switches the electronic shutter to OPEN during incidence of the falling components of the surface reflection component and the inside dispersion component. The control circuit 114 maintains this OPEN state of the electronic shutter in a period corresponding to a light emission pulse width, and then switches the electronic shutter to CLOSE again. Afterward, the next pulsed light beam is emitted, and the same operation is performed. Repeating the above-described operation removes the surface reflection component, thereby making it possible to efficiently detect the inside dispersion component that passes through a brain.

A time from the start of light emission to switching of the electronic shutter from CLOSE to OPEN can be determined before starting detection. For example, it is possible to measure a time from the start of light emission to the arrival of the rear end of the surface reflection component at the image sensor 113, by performing preliminary emission of light with the first light source 103 and detecting this light with the image sensor 113, before the start of detection. This measured time may be set as the time from the start of light emission to switching of the electronic shutter to OPEN.

Since the object 102 is the forehead of a person and the attenuation factor of light in the inside is very large when detecting information such as information indicating a cerebral blood flow, a light amount may be short to detect only the inside dispersion component if the light amount corresponds to emission of only one pulse. For this reason, in this embodiment, a pulsed light beam is emitted multiple times, and exposure is accordingly performed by the electronic shutter of the image sensor 113 multiple times. The detection signal is thereby multiplied, which makes it possible to enhance the sensitivity. However, depending on an intended use, it may not be necessary to perform each of light emission and exposure multiple times. In that case, light emission and exposure are performed once per frame, for each of the light sources.

FIGS. 7A and 7B are system timing diagrams each illustrating an example of operation of the imaging apparatus 101 in this embodiment. In FIGS. 7A and 7B, the signal A indicates a waveform of a pulsed light beam emitted by the first light source 103. The signal E indicates a timing of each of OPEN and CLOSE of the electronic shutter. A signal F indicates a timing of each of ON (i.e., a state where the charge is accumulated in the floating diffusion layer) and OFF (i.e., a state where the charge is not accumulated in the floating diffusion layer) of the floating diffusion layer 404.

FIG. 7A exemplifies operation in a first frame period that is a period of acquiring an image signal of a first frame. The first frame period is a period in which imaging is performed using the first light source 103 that emits light having the wavelength of 750 nm. The control circuit 114 first causes the first light source 103 to perform light emission multiple times in a predetermined cycle, and then causes the floating diffusion layer 404 to accumulate the signal charge in synchronization with the light emission. The signal charge accumulated in the floating diffusion layer 404 in the first frame period is used for generation of an image based on the rising component of the pulsed light beam having the wavelength of 750 nm, which is reflected from the object 102.

FIG. 7B exemplifies operation in a second frame period that is a period of acquiring an image signal of a second frame. The second frame period is a period in which imaging is performed using the first light source 103 that emits light having the wavelength of 750 nm. The control circuit 114 causes the first light source 103 to perform light emission multiple times in a predetermined cycle, and then causes the floating diffusion layer 404 to accumulate the signal charge in synchronization with the light emission. The signal charge accumulated in the floating diffusion layer 404 in the second frame period is used for generation of an image based on the falling component of the pulsed light beam having the wavelength of 750 nm, which is reflected from the object 102. This operation is described in further detail below.

The control circuit 114 first causes the first light source 103, which emits the light having the wavelength of 750 nm, to emit a pulsed light beam multiple times. For example, the control circuit 114 causes the first light source 103 to emit a pulsed light beam having a pulse width of about 10 ns, repeatedly around 1000 times at a frequency of about 10 MHz for a period of the order of about 100 μsec. While the light emission of the first light source 103 is repeated, the floating diffusion layer 404 is in an active (a low potential) state. In this state, each of the OPEN state and the CLOSE state of the electronic shutter is switched in synchronization with the light emission of the first light source 103. To be more specific, in the first frame period, the control circuit 414 in the image sensor 113 makes the potential of the drain 402 relatively high to cause the electronic shutter to be OPEN (the drain 402 is inactive) only in the period when the rising component of a pulsed light beam returning from the object 102 enters the photodiode 403.

In a period other than this period, the control circuit 414 makes the potential of the drain 402 relatively low to cause the electronic shutter to be CLOSE (the drain 402 is active). The signal charge generated in the photodiode 403 due to the rising component of a pulsed light beam from the object 102 is repeatedly accumulated in the floating diffusion layer 404 by such control. The image sensor 113 generates a pixel signal from the accumulated signal charge and transmits the generated pixel signal to the signal processing circuit 115. The signal processing circuit 115 generates an image from the signal of each pixel and stores the generated image into an internal memory and the like. This generated image corresponds to image information indicating a shallow part of a living body such as scalp and a skull.

In the second frame period, the control circuit 414 in the image sensor 113 first illuminates the object 102 with a pulsed light beam, and makes the potential of the drain 402 relatively low to cause the electronic shutter to be CLOSE. In a period when the falling component of a pulsed light beam from the object 102 enters the photodiode 403, the control circuit 414 makes the potential of the drain 402 relatively high to cause the electronic shutter to be OPEN (the drain 402 is inactive). Thereafter, the control circuit 414 makes the potential of the drain 402 relatively low to cause the electronic shutter to be CLOSE. In a period other than this period, the control circuit 414 makes the potential of the drain 402 relatively low to cause the electronic shutter to be CLOSE (the drain 402 is active).

The signal charge generated in the photodiode 403 due to the falling component of a pulsed light beam from the object 102 is repeatedly accumulated in the floating diffusion layer 404 by such control. The image sensor 113 forwards the accumulated signal charge to the signal processing circuit 115. The image sensor 113 generates the pixel signal from the accumulated signal charge and transmits the generated pixel signal to the signal processing circuit 115. The signal processing circuit 115 generates frame data from the signal of each pixel. This generated image corresponds to image information indicating both a shallow part of a living body such as scalp and a skull as well as a deep part of the living body such as a brain. Through the above-described processing, the signal processing circuit 115 generates frame data of each of the rising component and the falling component of a pulsed light beam reflected from the living body.

Figure 7C:
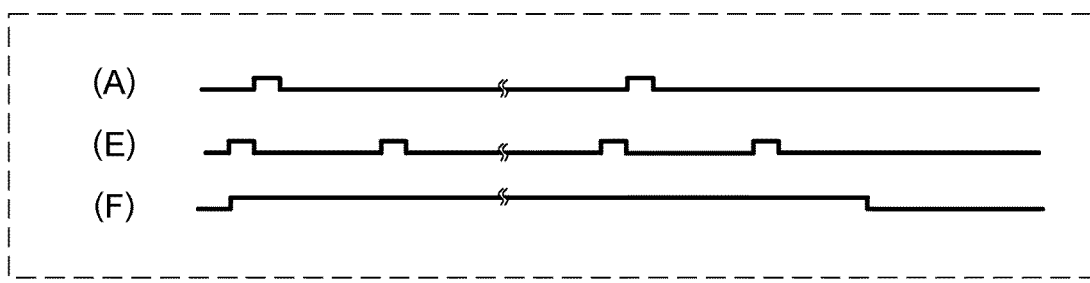
FIG. 7C is a timing diagram illustrating a modification of operation of the imaging apparatus in a period of acquiring an image signal of a first frame period in Embodiment 1.
Figure 7D:
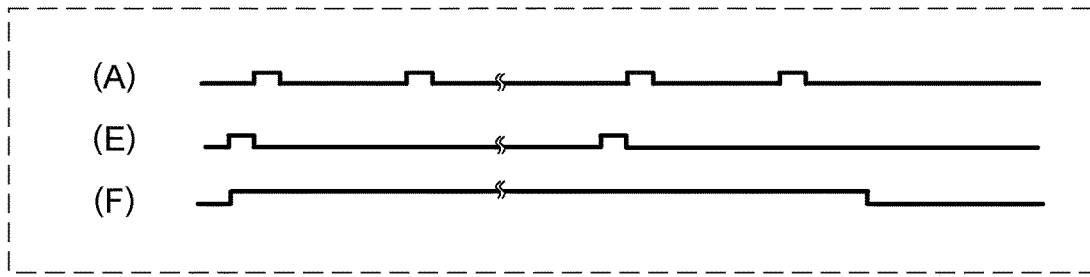
FIG. 7D is a timing diagram illustrating a modification of operation of the imaging apparatus in the period of acquiring an image signal of the first frame period in Embodiment 1.

In FIGS. 7A and 7B, an example in which the number of times of light emission that is the number of a pulsed light beam emitted by the first light source 103 and the number of times of exposure that is the number of times that the electronic shutter is caused to be in the OPEN state are the same is illustrated; however, it is not limited thereto. FIGS. 7C and 7D are timing diagrams each illustrating a modification of operation of an imaging apparatus in a period of acquiring an image signal of the first frame period in Embodiment 1.

As indicated by the signal D in FIG. 3, in the waveform of a reflected pulsed light beam detected by the image sensor 113, which is a light detector, the slope of the rising period is steeper than that of the falling period. Thus, when shutter widths are the same, in one pulse, an amount of signals detected in the rising period is greater than an amount of signals detected in the falling period. This allows the amount of signals detected in the rising period to be easily saturated by multiplying these signal amounts. In view of this, as the modification illustrated in FIG. 7C, the number of times of light emission in the first frame period may be smaller than that in FIG. 7A. In addition, as the modification illustrated in FIG. 7D, the number of times of exposure in the first frame period may be smaller than that in FIG. 7A.

3. Computation of Image

The signal of the rising component and the signal of the falling component are transmitted from the image sensor 113 to the signal processing circuit 115 and accumulated in each frame. The signal of the rising component mainly includes information indicating a change in a skin blood flow, while the signal of the falling component includes information indicating changes in a skin blood flow and a cerebral blood flow. Thus, in order to extract only information indicating a change in a cerebral blood flow, it is only necessary to separate the information indicating a change in a skin blood flow and the information indicating a change in a cerebral blood flow by using these signals.

The present inventors focus on that both a change in a skin blood flow and a change in a cerebral blood flow are accompanied by an vasodilatation and vasoconstriction activity of a blood vessel or a capillary, and distributions of blood vessels in each of skin and brain are different. The present inventors thus consider that the distribution of a change in a skin blood flow and the distribution of a change in a cerebral blood flow are in an uncorrelated relationship. Based on this thought, an image of a change in a skin blood flow and an image of a change in a cerebral blood flow are separated by computation that uses signals respectively reflected on the image formed from the signal of the rising component and the image formed from the signal of the falling component. Details of this separation are described below.

The signal of the rising component and the signal of the falling component respectively include information indicating a change in a skin blood flow and information indicating a change in a cerebral blood flow at a different ratio, which is represented by the following theoretical formula (1):

$$\begin{pmatrix} Sr \\ Sf \end{pmatrix} = \begin{pmatrix} a & b \\ c & d \end{pmatrix} \begin{pmatrix} Ss \\ Sb \end{pmatrix}. \tag{1}$$

Here, Sr and Sf respectively represent the rising component and the falling component of a reflected pulsed light beam. Each of a, b, c, and d represents a coefficient. Ss and Sb respectively represent a component of a change in a skin blood flow and a component of a change in a cerebral blood flow. In other words, the left member is a known pixel signal value that is detected by the image sensor, while the right member is an unknown.

For example, assuming that the rising component is composed of the component of a change in a skin blood flow, a=1, b=0, and Ss=Sr are plugged in, while each of c, d, and Sb is an unknown. In this case, there are many combinations of unknowns that make the left member and the right member equal to each other. Taking advantage of the uncorrelation between the distribution of a change in a skin blood flow and the distribution of a change in a cerebral blood flow, the coefficients c and d and a value of Sb that make a correlation coefficient in each of all pixel components of a change in a skin blood flow Ss and a change in a cerebral blood flow Sb be the correlation coefficient closest to zero are extracted. Thus obtained signals of Ss and Sb respectively indicate a change in a skin blood flow and a change in a cerebral blood flow.

The above description is given with a condition that the rising component is equal to the component of a change in a skin blood flow; however, since the rising component may include a few amount of a cerebral blood flow, a and b may be used as variables.

In the formula (1), correlativity of the distribution of a change in a skin blood flow and the distribution of a change in a cerebral blood flow is used to obtain a coefficient; however, a multivariate analysis such as an independent component analysis may be used. Or, a, b, c, and d that are optimum for separating a change in a skin blood flow and a change in a cerebral blood flow may be obtained in advance by using a phantom having an optical property that is similar to that of a human.

A change in a skin blood flow and a change in a cerebral blood flow are considered that they are continuously changed temporally. That is, correlativity between the frames is considered to be high. In addition to the formula (1), Ss and Sb that satisfy the formula (1) may be accurately obtained by also obtaining the correlativity between the frames and a motion vector for each pixel.

Performing this image computation makes it possible to cut out a change in a skin blood flow and a change in a cerebral blood flow into different images from the component of a change in a skin blood flow and the component of a change in a cerebral blood flow that are respectively included in the rising component and the falling component at a different ratio.

Image processing is performed in the signal processing circuit 115 in this embodiment; however, image processing may be performed by using an external computer and a computation processing circuit.

In addition, an example in which the image sensor is used as a light detector is described in this embodiment; however, it is not limited thereto. As a light detector, a combination of an avalanche photodiode and a memory, or a combination of a PIN photodiode and a memory may be used. Even in a case of using the combination of an avalanche photodiode and a memory or the combination of a PIN photodiode and a memory as a light detector, it is possible to obtain an enough amount of signals by detecting the rising component and the falling component of reflected light of each pulse and repeatedly accumulating the detected components in a memory, for example. Computing the amount of signals accumulated in the memory according to the formula (1) makes it possible to separate a change in a skin blood flow and a change in a cerebral blood flow.

Embodiment 2

Next, an imaging apparatus 201 in Embodiment 2 of the present disclosure is described. This embodiment is different from Embodiment 1 in using two light sources that each emits a pulsed light beam having a wavelength different from each other. Using the imaging apparatus 201 in Embodiment 2, an example of obtaining information on hemoglobin in a blood pressure is described. Descriptions are given below focusing on these points different from Embodiment 1.

Figure 8:
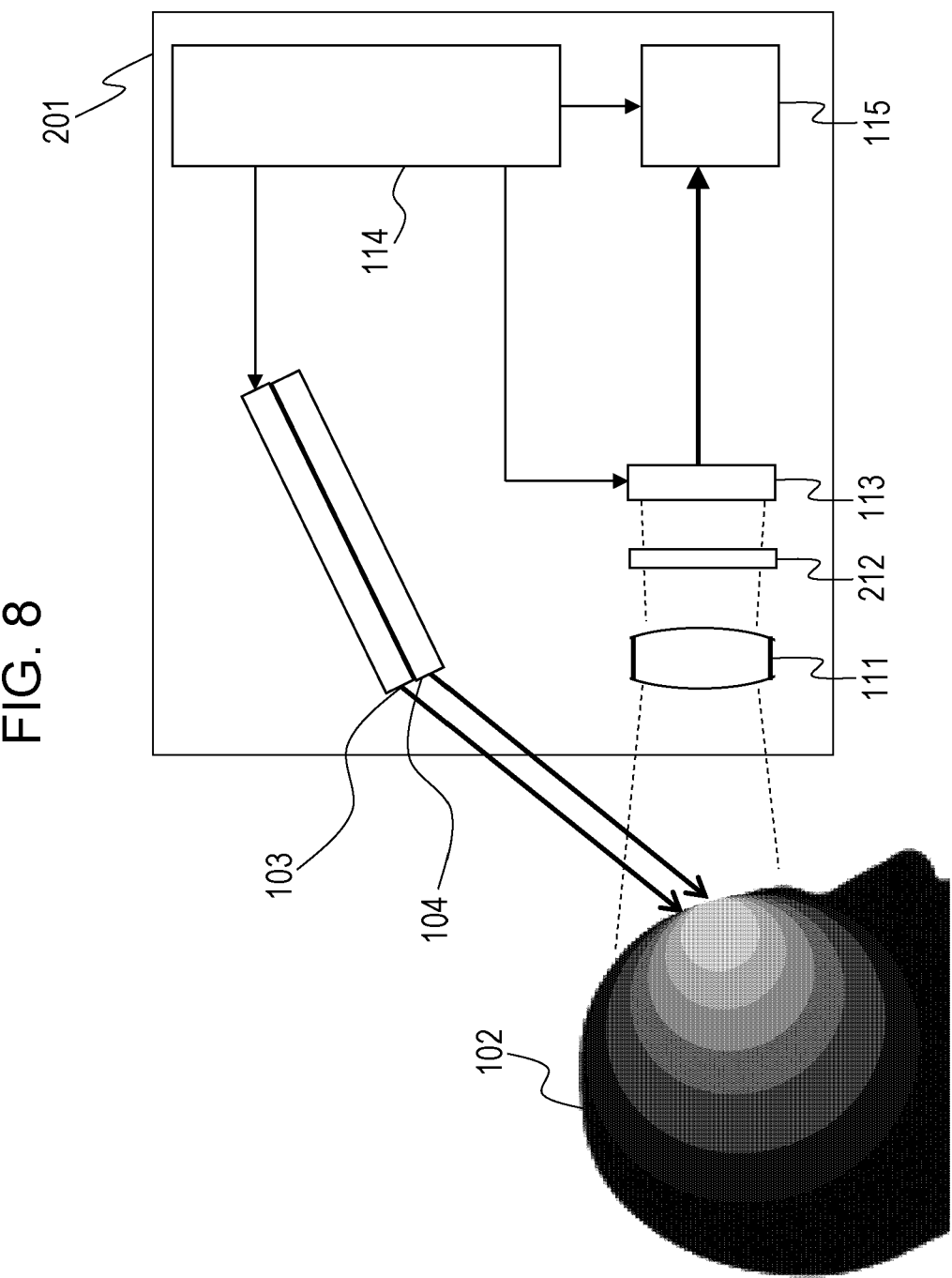
FIG. 8 is a diagram schematically illustrating an image sensor and an optical system in an imaging apparatus of Embodiment 2.

FIG. 8 is a diagram schematically illustrating a configuration of the imaging apparatus 201 in this embodiment. The imaging apparatus 201 includes the first light source 103, a second light source 203, the image sensor 113, a double band-pass filter 212, the optical system 111, the control circuit 114, and the signal processing circuit 115. Each of the first light source 103 and the second light source 203 emits a pulsed light beam toward a point where the object 102 is located. In this embodiment, the first light source 103 is a laser light source that emits a narrow-band pulsed light beam having a center wavelength of 750 nm, while the second light source 203 is a laser light source that emits a narrow-band pulsed light beam having a center wavelength of 850 nm. The double band-pass filter 212 is disposed between the optical system 111 and the image sensor 113 and mainly allows only light having a wavelength corresponding to the wavelength of a ray from the first light source 103 or the second light source 203 to pass therethrough. The control circuit 114 is connected to the first light source 103, the second light source 203, and the image sensor 113, and controls operation of these components. To be more specific, the control circuit 114 performs control, by synchronizing a light emission timing of the first light source 103 and the second light source 203 with a timing of signal accumulation and signal discharge of each pixel of the image sensor 113. This makes it possible to detect information indicating a scalp blood flow and a cerebral blood flow in a living body with high accuracy and, particularly, to detect an amount of changes in oxygenated hemoglobin and deoxygenated hemoglobin contained in a blood flow.

Figure 9:
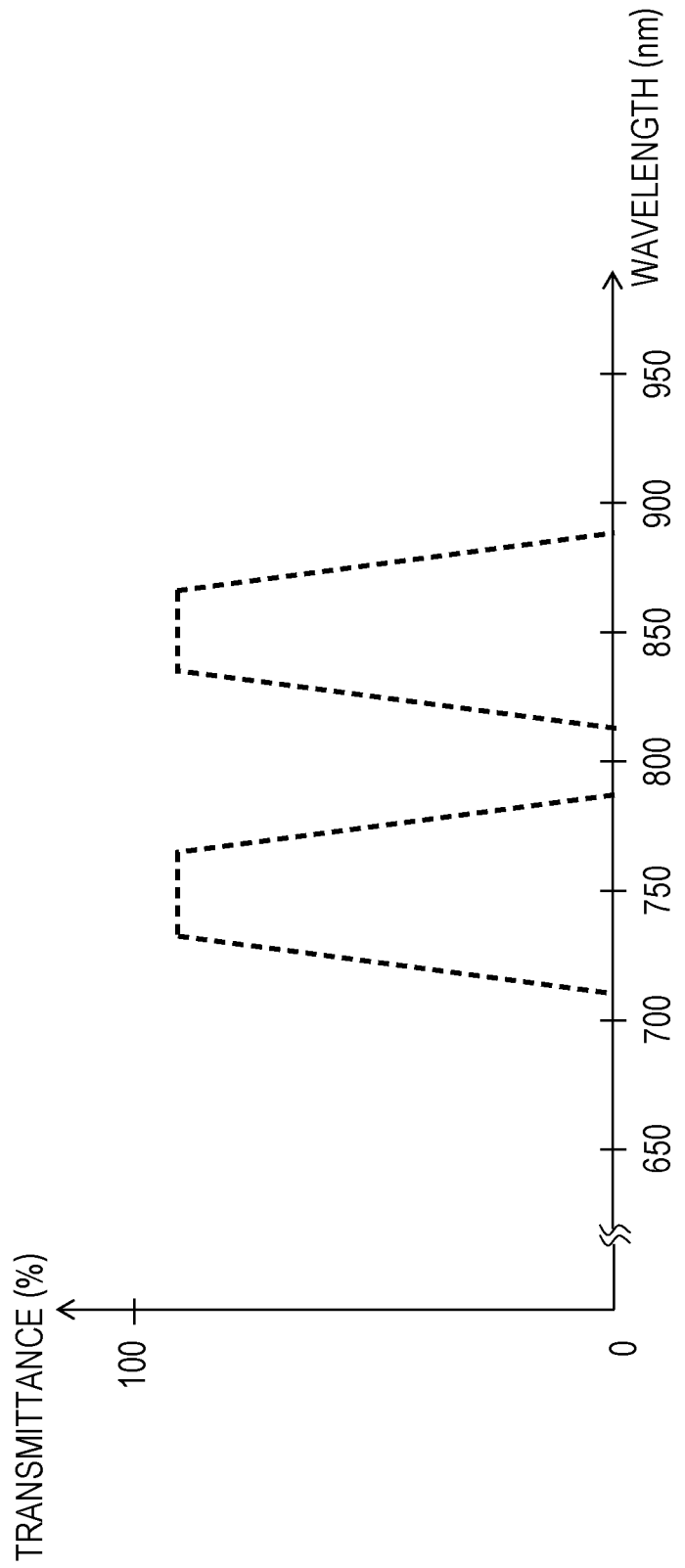
FIG. 9 is a diagram illustrating an example of spectral transmittance of a double band-pass filter in Embodiment 2.

FIG. 9 is a graph illustrating an example of spectral transmittance of the double band-pass filter 212. As illustrated in the drawing, the double band-pass filter 212 allows narrow-band light having a center wavelength of 750 nm that is emitted by the first light source 103 and narrow-band light having a center wavelength of 850 nm that is emitted by the second light source 203 to pass therethrough while blocking light having different wavelength. It is possible to suppress disturbance light (e.g., background light) from entering the image sensor 113, by disposing the double band-pass filter 212 described above.

FIGS. 10A to 10D are timing diagrams each illustrating an example of operation of the imaging apparatus 201 in this embodiment. In FIGS. 10A to 10D, a signal A1 indicates a waveform of a pulsed light beam emitted by the first light source 103. A signal A2 indicates a waveform of a pulsed light beam emitted by the second light source 203. The signal E indicates a timing of each of OPEN and CLOSE of the electronic shutter. A signal F indicates a timing of each of ON (i.e., a state where the charge is accumulated in the floating diffusion layer) and OFF (i.e., a state where the charge is not accumulated in the floating diffusion layer) of the floating diffusion layer 404.

Figure 10A:
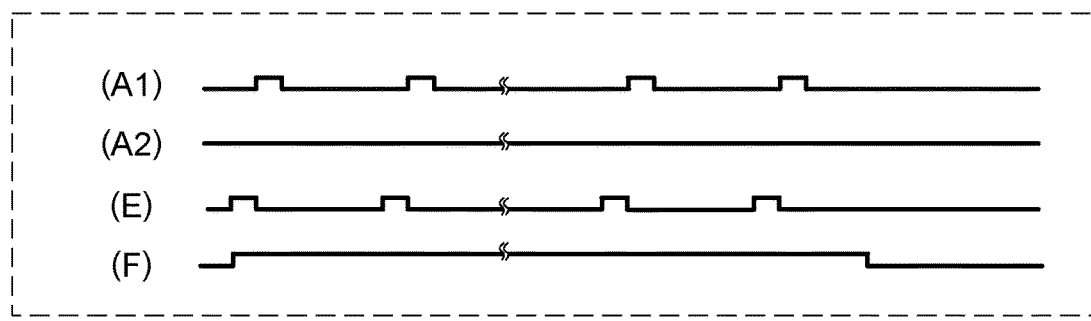
FIG. 10A is a timing diagram illustrating an example of operation of the imaging apparatus in a period of acquiring an image signal of a first frame period in Embodiment 2.

FIG. 10A exemplifies operation in a first frame period that is a period of acquiring an image signal of a first frame. The first frame period is a period in which imaging is performed using the first light source 103 that emits light having the wavelength of 750 nm. The control circuit 114 first causes the first light source 103 to perform light emission multiple times in a predetermined cycle, and then causes the floating diffusion layer 404 to accumulate the signal charge in synchronization with the light emission. The signal charge accumulated in the floating diffusion layer 404 in the first frame period is used for generation of an image based on the rising component of a pulsed light beam having the wavelength of 750 nm, which is reflected from the object 102.

Figure 10B:
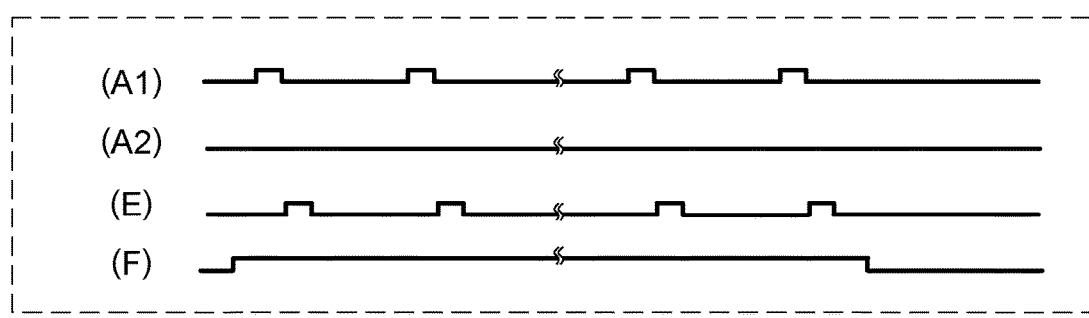
FIG. 10B is a timing diagram illustrating an example of operation of the imaging apparatus in a period of acquiring an image signal of a second frame period in Embodiment 2.

FIG. 10B exemplifies operation in a second frame period that is a period of acquiring an image signal of a second frame. The second frame period is a period in which imaging is performed using the first light source 103 that emits light having the wavelength of 750 nm. The control circuit 114 causes the first light source 103 to perform light emission multiple times in a predetermined cycle, and then causes the floating diffusion layer 404 to accumulate the signal charge in synchronization with the light emission. The signal charge accumulated in the floating diffusion layer 404 in the second frame period is used for generation of an image based on the falling component of a pulsed light beam having the wavelength of 750 nm, which is reflected from the object 102.

Figure 10C:
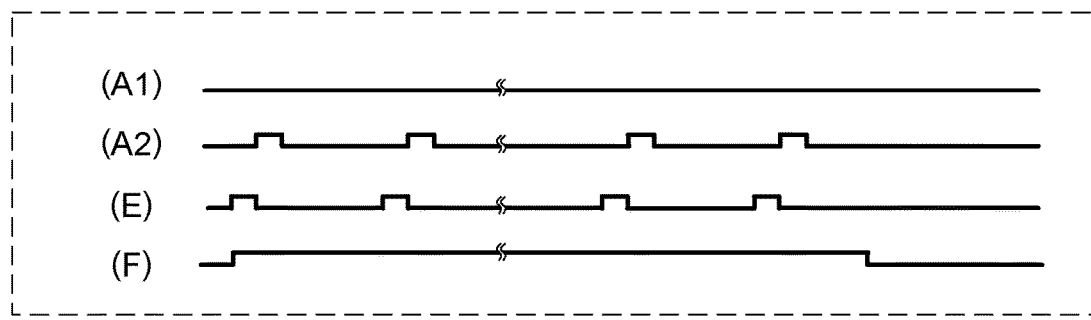
FIG. 10C is a timing diagram illustrating an example of operation of the imaging apparatus in a period of acquiring an image signal of a third frame period in Embodiment 2.

FIG. 10C exemplifies operation in a third frame period that is a period of acquiring an image signal of a third frame. The third frame period is a period in which imaging is performed using the second light source 203 that emits light having the wavelength of 850 nm. The control circuit 114 first causes the second light source 203 to perform light emission multiple times in a predetermined cycle, and then causes the floating diffusion layer 404 to accumulate the signal charge in synchronization with the light emission. The signal charge accumulated in the floating diffusion layer 404 in the third frame period is used for generation of an image based on the rising component of a pulsed light beam having the wavelength of 850 nm, which is reflected from the object 102.

Figure 10D:
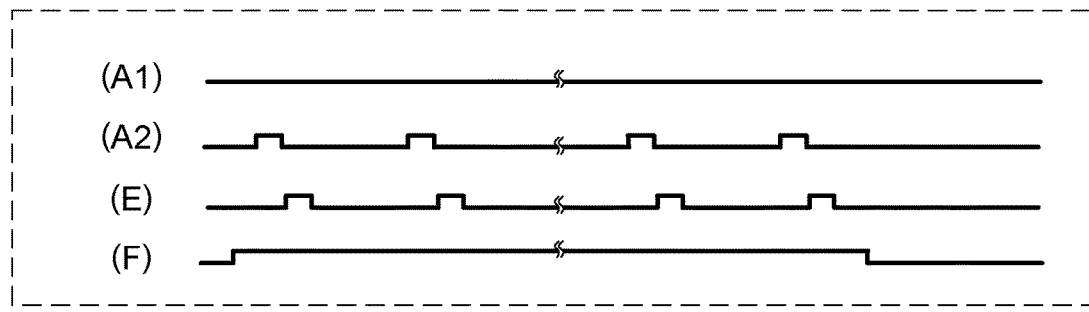
FIG. 10D is a timing diagram illustrating an example of operation of the imaging apparatus in a period of acquiring an image signal of a fourth frame period in Embodiment 2.

FIG. 10D exemplifies operation in a fourth frame period that is a period of acquiring an image signal of a fourth frame. The fourth frame period is a period in which imaging is performed using the second light source 203 that emits light having the wavelength of 850 nm. The control circuit 114 causes the second light source 203 to perform light emission multiple times in a predetermined cycle, and then causes the floating diffusion layer 404 to accumulate the signal charge in synchronization with the light emission. The signal charge accumulated in the floating diffusion layer 404 in the fourth frame period is used for generation of an image based on the falling component of a pulsed light beam having the wavelength of 850 nm, which is reflected from the object 102.

The signal of the rising component and the signal of the falling component are transmitted from the image sensor 113 to the signal processing circuit 115 and accumulated in each frame. The signal of the rising component mainly includes image data of a wavelength of 750 nm, while the signal of the falling component includes image data of a wavelength of 850 nm. Since absorption coefficients for a wavelength of oxygenated hemoglobin and a wavelength of deoxygenated hemoglobin are generally known, it is possible to calculate an amount of oxygenated hemoglobin and an amount of deoxygenated hemoglobin in the rising component and the falling component based on the image data of two different types of wavelengths. Because both the rising component and the falling component include a skin blood flow and a cerebral blood flow in which hemoglobin is contained at a different ratio, it is only necessary to separate these flow rates. The separation can be performed in the same way as that in Embodiment 1; thus, a description thereof is omitted.

As described above, the imaging apparatus 201 in this embodiment includes the first light source 103 and the second light source 203, which emit a pulsed light beam onto the object 102, the image sensor 113, the control circuit 114, and the signal processing circuit 115. The image sensor 113 has pixels. Each of the pixels has the photodiode 403 and the floating diffusion layer 404 as an accumulator. The first light source 103 emits a pulsed light beam having a first wavelength range (e.g., a wavelength range around 750 nm).

The second light source 203 emits a pulsed light beam having a second wavelength range (e.g., a wavelength range around 850 nm). The control circuit 114 controls a timing when a pulsed light beam is emitted by the first light source 103, a timing when a pulsed light beam is emitted by the second light source 203, a timing when the signal charge is accumulated in the floating diffusion layer 404, and a timing when the signal charge is discharged. The control circuit 114 performs the following operation.

(1) In the first frame period, causing the first light source 103 to emit a pulsed light beam.

(2) In a period including at least part of the rising period that is a period when the surface reflection component I1 of a pulsed light beam emitted by the first light source 103 enters the image sensor 113 after being reflected mainly from a surface of the object 102, accumulating the signal charge in the floating diffusion layer 404 by causing the image sensor 113 to be a state where the signal charge is accumulated in the floating diffusion layer 404 and to be a state where the signal charge is not discharged.

(3) In the second frame period, causing the first light source 103 to emit a pulsed light beam.

(4) After the rear end of the surface reflection component I1 of a pulsed light beam emitted by the first light source 103 enters the image sensor 113, in a period when the internal dispersion component I2 is returned to enter the image sensor 113 after being dispersed mainly in the object 102, accumulating the signal charge in the floating diffusion layer 404 by causing the image sensor 113 to be a state where the signal charge is accumulated in the floating diffusion layer 404 and to be a state where the signal charge is not discharged.

(5) In the third frame period, causing the second light source 203 to emit a pulsed light beam.

(6) In a period including at least part of the rising period that is a period when the surface reflection component I1 of a pulsed light beam emitted by the second light source 203 enters the image sensor 113 after being reflected mainly from the surface of the object 102, accumulating the signal charge in the floating diffusion layer 404 by causing the image sensor 113 to be a state where the signal charge is accumulated in the floating diffusion layer 404 and to be a state where the signal charge is not discharged.

(7) In the fourth frame period, causing the second light source 203 to emit a pulsed light beam.

(8) After the rear end of the surface reflection component I1 of a pulsed light beam emitted by the second light source 203 enters the image sensor 113, in a period when the internal dispersion component I2 is returned to enter the image sensor 113 after being dispersed mainly in the object 102, accumulating the signal charge in the floating diffusion layer 404 by causing the image sensor 113 to be a state where the signal charge is accumulated in the floating diffusion layer 404 and to be a state where the signal charge is not discharged.

The signal processing circuit 115 calculates an amount of oxygenated hemoglobin and an amount of deoxygenated hemoglobin in the rising component based on the image signal in the first frame period and the image signal in the third frame period. The signal processing circuit 115 also calculates an amount of oxygenated hemoglobin and an amount of deoxygenated hemoglobin in the falling component based on the image signal in the second frame period and the image signal in the fourth frame period. Thereafter, the signal processing circuit 115 obtains a distribution of a change in concentration of hemoglobin in each of a skin blood flow and a cerebral blood flow by image computation.

According to the above configuration and operation, detecting the rising component and the falling component of a pulsed light beam reflected from a living body for each frame makes it possible to obtain a distribution of a change in hemoglobin in each of a skin blood flow and a cerebral blood flow.

Light having two types of wavelengths is used in this embodiment; however, light having three or more types of wavelength may be used.

Embodiment 3

Next, the imaging apparatus 201 in Embodiment 3 of the present disclosure is described. This embodiment is different from Embodiments 1 and 2 in detecting reflected light having wavelengths in one frame period by providing accumulators included in one pixel, or in detecting the rising component and the falling component in one frame period. Descriptions are given below focusing on these points different from Embodiments 1 and 2.

Figure 11:
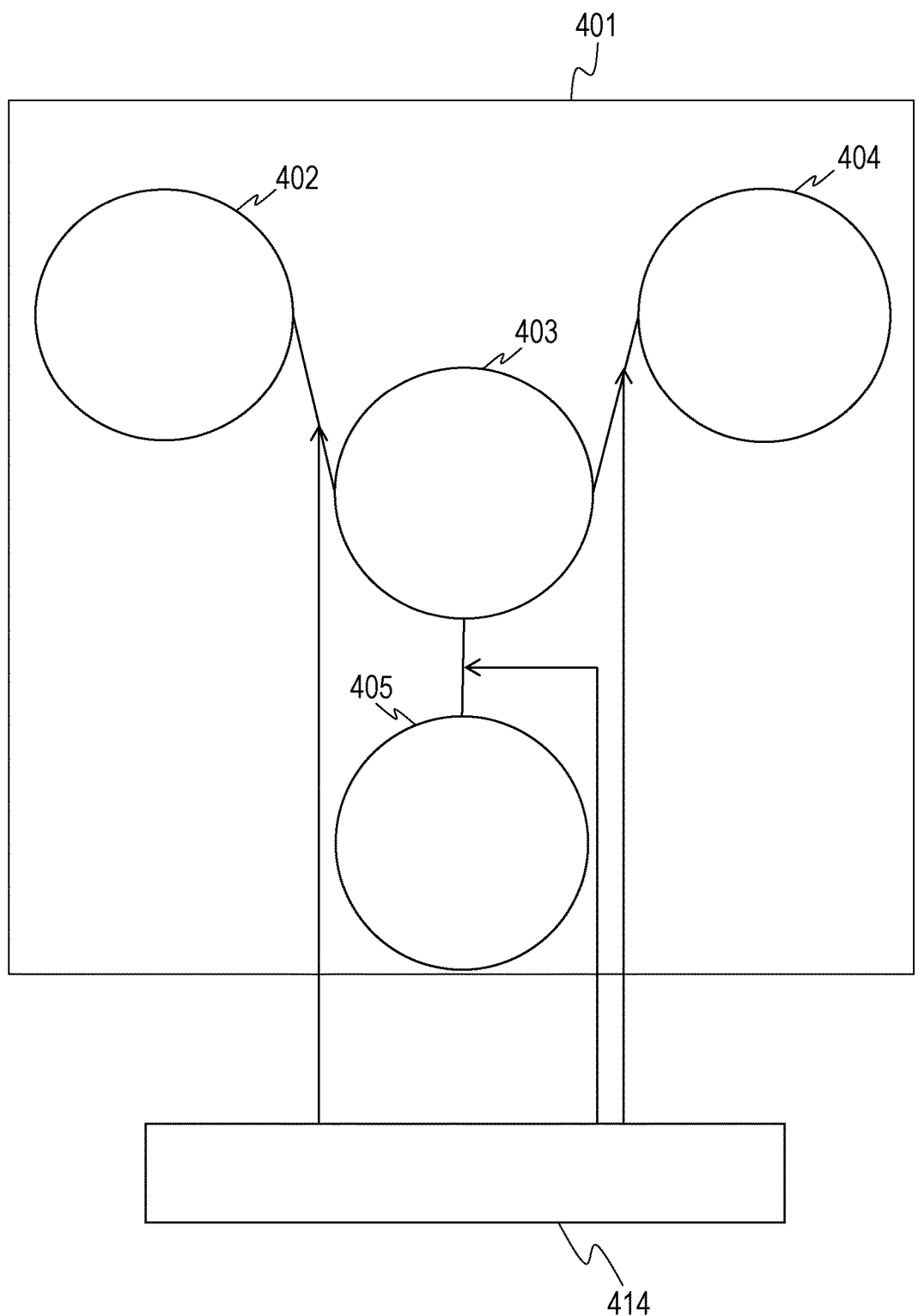
FIG. 11 is a diagram illustrating in a simple manner a configuration of one of pixels in an image sensor in Embodiment 3.

FIG. 11 is a diagram illustrating a schematic configuration of one of the pixels 401 of the image sensor 113. Note that FIG. 11 schematically illustrates the configuration of one of the pixels 401, and does not necessarily reflect a real structure. The pixel 401 includes the photodiode 403, which performs photoelectric conversion, two floating diffusion layers 404 and 405, each of which is an accumulator that accumulates the signal charge, and the drain 402, which discharges the signal charge. Functions of the floating diffusion layers 404 and 405 and the drain 402 are the same as the functions already described with reference to FIG. 2.

The image sensor 113 includes the control circuit 414 that controls accumulation and discharge of the signal charge in each of the pixels 401, based on a command from the control circuit 114. The control circuit 414 can be a circuit (e.g., a microcontroller unit) having a processor and a memory. In accordance with a control program stored in the memory, the control circuit 414 controls accumulation of the signal charge to the floating diffusion layers 404 and 405, and discharge of the signal charge to the drain 402, in response to an instruction from the control circuit 114 externally provided.

The light that enters each of the pixels 401 as a result of light emission of one pulse is converted by the photodiode 403 into signal electrons that are the signal charge. The signal electrons resulting from the conversion are discharged to the drain 402, or distributed to either of the floating diffusion layers 404 and 405, in accordance with a control signal inputted from the control circuit 414.

Figure 12A:
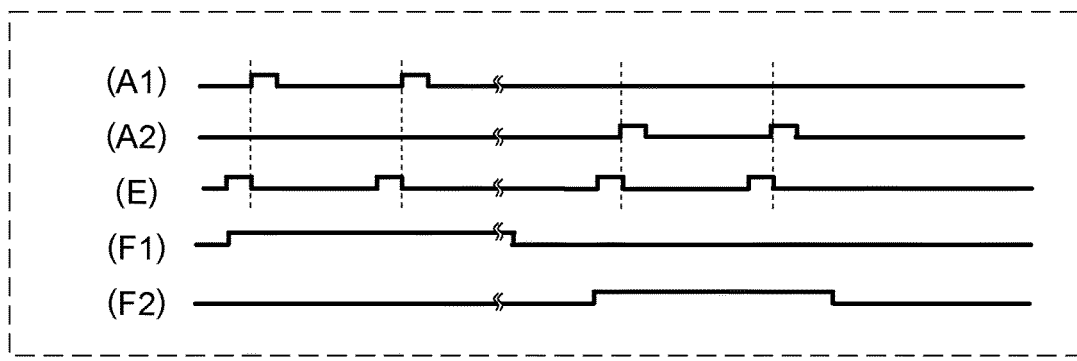
FIG. 12A is a timing diagram illustrating an example of operation of an imaging apparatus in a period of acquiring an image signal of a first frame period in Embodiment 3.
Figure 12B:
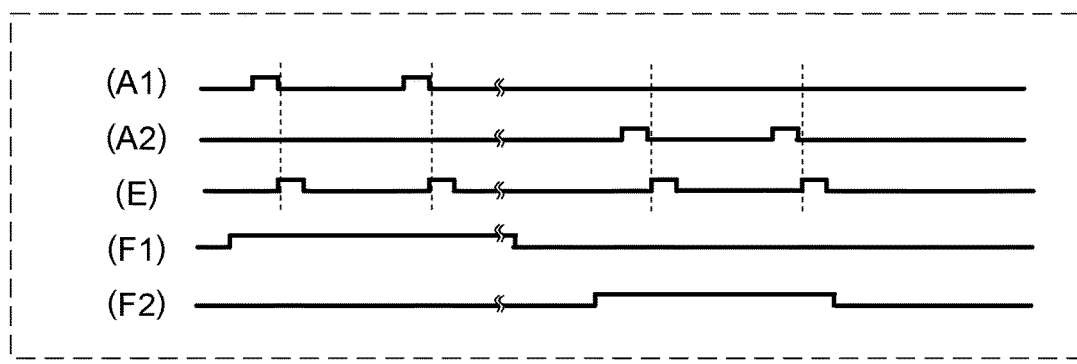
FIG. 12B is a timing diagram illustrating an example of operation of an imaging apparatus in a period of acquiring an image signal of a second frame period in Embodiment 3.

FIGS. 12A and 12B are timing diagrams each illustrating an example of operation of the imaging apparatus 201 in this embodiment. In FIGS. 12A and 12B, the signal A1 indicates a waveform of a pulsed light beam emitted by the first light source 103. The signal A2 indicates a waveform of a pulsed light beam emitted by the second light source 203. The signal E indicates a timing of each of OPEN and CLOSE of the electronic shutter. A signal F1 indicates a timing of each of ON (i.e., a state where the charge is accumulated in the floating diffusion layer) and OFF (i.e., a state where the charge is not accumulated in the floating diffusion layer) of the floating diffusion layer 404. A signal F2 indicates a timing of each of ON and OFF of the floating diffusion layer 405.

FIG. 12A exemplifies operation in a first frame period that is a period of acquiring an image signal of a first frame. The first frame period is a period in which imaging is performed using the first light source 103 that emits light having the wavelength of 750 nm and the second light source 203 that emits light having the wavelength of 850 nm. The control circuit 114 first causes the first light source 103 to perform light emission multiple times in a predetermined cycle, and then causes the floating diffusion layer 404 to accumulate the signal charge in synchronization with the light emission. The control circuit 114 then causes the second light source 203 to perform light emission multiple times in a predetermined cycle, and then causes the floating diffusion layer 405 to accumulate the signal charge in synchronization with the light emission. The signal charge accumulated in the floating diffusion layers 404 and 405 in the first frame period is used for generation of an image based on each of the rising components of a pulsed light beam having the wavelength of 750 nm and 850 nm, which is reflected from the object 102.

FIG. 12B exemplifies operation in a second frame period that is a period of acquiring an image signal of a second frame. The second frame period is a period in which imaging is performed using the first light source 103 that emits light having the wavelength of 750 nm and the second light source 203 that emits light having the wavelength of 850 nm. The control circuit 114 first causes the first light source 103 to perform light emission multiple times in a predetermined cycle, and then causes the floating diffusion layer 404 to accumulate the signal charge in synchronization with the light emission. The control circuit 114 then causes the second light source 203 to perform light emission multiple times in a predetermined cycle, and then causes the floating diffusion layer 405 to accumulate the signal charge in synchronization with the light emission. The signal charge accumulated in the floating diffusion layers 404 and 405 in the second frame period is used for generation of an image based on each of the falling components of a pulsed light beam having the wavelength of 750 nm and 850 nm, which is reflected from the object 102.

The signal of the rising component accumulated in the floating diffusion layer 404 and the signal of the falling component accumulated in the floating diffusion layer 405 are transmitted from the image sensor 113 to the signal processing circuit 115. The signal of the rising component includes image data of a wavelength of 750 nm, while the signal of the falling component includes image data of a wavelength of 850 nm. Since absorption coefficients for a wavelength of oxygenated hemoglobin and a wavelength of deoxygenated hemoglobin are generally known, it is possible to calculate an amount of oxygenated hemoglobin and an amount of deoxygenated hemoglobin in the rising component and the falling component, respectively, based on the image data of two different types of wavelengths. Because both the rising component and the falling component include a skin blood flow and a cerebral blood flow in which hemoglobin is contained at a different ratio, it is only necessary to separate these flow rates. The separation can be performed in the same way as that in Embodiment 1; thus, a description thereof is omitted.

As described above, the imaging apparatus 201 in this embodiment includes the first light source 103 and the second light source 203, which emit a pulsed light beam onto the object 102, the image sensor 113, the control circuit 114, and the signal processing circuit 115. The image sensor 113 has pixels. Each of the pixels has the photodiode 403 and the floating diffusion layers 404 and 405. The first light source 103 emits a pulsed light beam having a first wavelength range (e.g., a wavelength range around 750 nm). The second light source 203 emits a pulsed light beam having a second wavelength range (e.g., a wavelength range around 850 nm). The control circuit 114 controls a timing when a pulsed light beam is emitted by the first light source 103, a timing when a pulsed light beam is emitted by the second light source 203, a timing when the signal charge is accumulated in the floating diffusion layer 404, a timing when the signal charge is accumulated in the floating diffusion layer 405, and a timing when the signal charge is discharged. The control circuit 114 performs the following operation.

(1) In the first frame period, causing the first light source 103 to emit a pulsed light beam and sequentially causing the second light source 203 to emit a pulsed light beam.

(2) In a period including at least part of the rising period that is a period when the surface reflection component I1 of a pulsed light beam emitted by the first light source 103 enters the image sensor 113 after being reflected mainly from the surface of the object 102, accumulating the signal charge in the floating diffusion layer 404 by causing the image sensor 113 to be a state where the signal charge is accumulated in the floating diffusion layer 404 and to be a state where the signal charge is not discharged. Then, in a period including at least part of the rising period of a pulsed light beam emitted by the second light source 203, accumulating the signal charge in the floating diffusion layer 405 by causing the image sensor 113 to be a state where the signal charge is accumulated in the floating diffusion layer 405 and to be a state where the signal charge is not discharged.

(3) In the second frame period, causing the first light source 103 to emit a pulsed light beam and sequentially causing the second light source 203 to emit a pulsed light beam.

(4) After the rear end of the surface reflection component I1 of a pulsed light beam emitted by the first light source 103 enters the image sensor 113, in a period when the internal dispersion component I2 is returned to enter the image sensor 113 after being dispersed in the object 102, accumulating the signal charge in the floating diffusion layer 404 by causing the image sensor 113 to be a state where the signal charge is accumulated in the floating diffusion layer 404 and to be a state where the signal charge is not discharged. Then, after the rear end of the surface reflection component I1 of a pulsed light beam emitted by the second light source 203 enters the image sensor 113, in a period when the internal dispersion component I2 is returned to enter the image sensor 113 after being dispersed in the object 102, accumulating the signal charge in the floating diffusion layer 405 by causing the image sensor 113 to be a state where the signal charge is accumulated in the floating diffusion layer 405 and to be a state where the signal charge is not discharged.

The signal processing circuit 115 calculates an amount of oxygenated hemoglobin and an amount of deoxygenated hemoglobin in the rising component based on the signal charge accumulated in the floating diffusion layer 404 and the signal charge accumulated in the floating diffusion layer 405 in the first frame period. The signal processing circuit 115 also calculates an amount of oxygenated hemoglobin and an amount of deoxygenated hemoglobin in the falling component based on the signal charge accumulated in the floating diffusion layer 404 and the signal charge accumulated in the floating diffusion layer 405 in the second frame period. Thereafter, the signal processing circuit 115 obtains a distribution of a change in concentration of hemoglobin in each of a skin blood flow and a cerebral blood flow by image computation.

According to the above configuration and operation, detecting the rising component and the falling component of a pulsed light beam reflected from a living body for each frame makes it possible to quickly obtain a distribution of a change in hemoglobin in each of a skin blood flow and a cerebral blood flow. This allows a frame rate in this embodiment to be faster than that in Embodiments 1 and 2.

This embodiment is described using the two floating diffusion layers; however, even in a case of using multi-wavelength, it is still possible to make the frame rate fast by performing the same operation while increasing the number of floating diffusion layers in accordance with increase of the number of wavelengths.

Embodiment 4

Next, the imaging apparatus 101 in Embodiment 4 of the present disclosure is described. In this embodiment, speeding up the control of the floating diffusion layer makes it possible to obtain the rising component and the falling component of a pulsed light beam reflected off the object 102 and a pulsed light beam emitted by the first light source 103 at almost the same timing. This allows a frame rate in this embodiment to be improved more than that in Embodiments 1 to 3.

A schematic configuration of the pixels is the same as that in FIG. 11. Note that FIG. 11 schematically illustrates the configuration of one of the pixels 401, and does not necessarily reflect a real structure. The pixel 401 includes the photodiode 403, which performs photoelectric conversion, the two floating diffusion layers 404 and 405, each of which is an accumulator that accumulates the signal charge, and the drain 402, which discharges the signal charge. Functions of the floating diffusion layers 404 and 405 and the drain 402 are the same as the functions already described with reference to FIG. 2.

The image sensor 113 includes the control circuit 414 that controls accumulation and discharge of the signal charge in each of the pixels 401, based on a command from the control circuit 114. The control circuit 414 can be a circuit (e.g., a microcontroller unit) having a processor and a memory. In accordance with a control program stored in the memory, the control circuit 414 controls accumulation of the signal charge to the floating diffusion layers 404 and 405, and discharge of the signal charge to the drain 402, in response to an instruction from the control circuit 114 externally provided.

The light that enters each of the pixels 401 as a result of light emission of one pulse is converted by the photodiode 403 into signal electrons that are the signal charge. The signal electrons resulting from the conversion are discharged to the drain 402, or distributed to either of the floating diffusion layers 404 and 405, in accordance with a control signal inputted from the control circuit 414.

Figure 13:
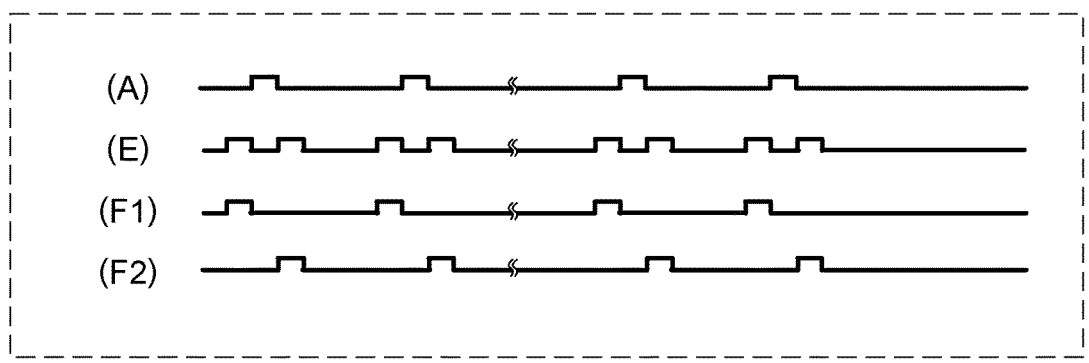
FIG. 13 is a timing diagram illustrating an example of operation of an imaging apparatus in Embodiment 4.

FIG. 13 is a timing diagram illustrating an example of operation of the imaging apparatus 101 in this embodiment. In FIG. 13, the signal A indicates a waveform of a pulsed light beam emitted by the first light source 103. The signal E indicates a timing of each of OPEN and CLOSE of the electronic shutter. The signal F1 indicates a timing of each of ON (i.e., a state where the charge is accumulated in the floating diffusion layer) and OFF (i.e., a state where the charge is not accumulated in the floating diffusion layer) of the floating diffusion layer 404. The signal F2 indicates a timing of each of ON and OFF of the floating diffusion layer 405.

In one frame period, imaging is performed by using the first light source 103 that emits light having a wavelength of 750 nm. The control circuit 114 causes the first light source 103 to perform light emission, and then causes the rising component of a pulsed light beam to be accumulated in the floating diffusion layer 404 in which operation is controlled to be high speed. Then, the control circuit 114 causes the falling component of a pulsed light beam to be accumulated in the floating diffusion layer 405 in which operation is controlled to be high speed. Repeating this operation multiple times within one frame allows the rising component and the falling component of a pulsed light beam reflected off the object 102 to be respectively accumulated in the floating diffusion layer 404 and in the floating diffusion layer 405, and they are used for generation of an image.

The image data transmitted from the image sensor 113 to the signal processing circuit 115 includes image data of the rising component accumulated in the floating diffusion layer 404 and image data of the falling component accumulated in the floating diffusion layer 405. Because both the rising component and the falling component include a skin blood flow and a cerebral blood flow in which hemoglobin is contained at a different ratio, it is only necessary to separate these flow rates. The separation can be performed in the same way as that in Embodiment 1; thus, a description thereof is omitted.

Figure 14:
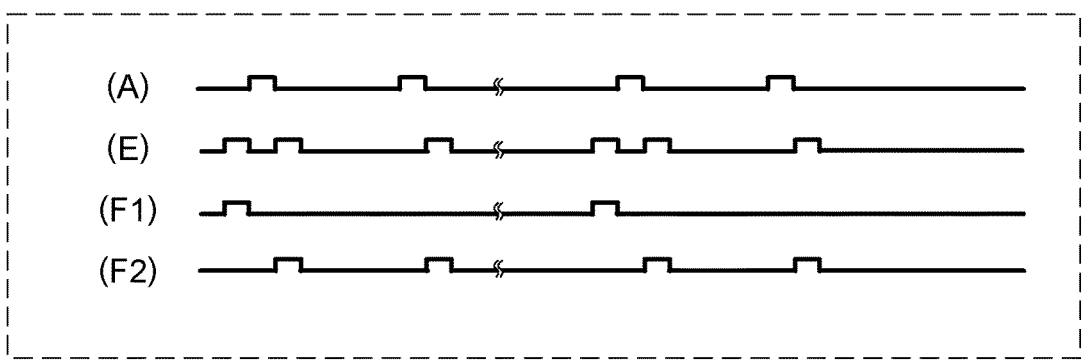
FIG. 14 is a timing diagram illustrating a modification of the operation of an imaging apparatus in Embodiment 4.

FIG. 14 is a timing diagram illustrating a modification of the operation of the imaging apparatus 101 in this embodiment. In FIG. 14, the signal A indicates a waveform of a pulsed light beam emitted by the first light source 103. The signal E indicates a timing of each of OPEN and CLOSE of the electronic shutter. The signal F1 indicates a timing of each of ON (i.e., a state where the charge is accumulated in the floating diffusion layer) and OFF (i.e., a state where the charge is not accumulated in the floating diffusion layer) of the floating diffusion layer 404. The signal F2 indicates a timing of each of ON and OFF of the floating diffusion layer 405.

As described in the modification of Embodiment 1 illustrated in FIGS. 7C and 7D, since the intensity of the rising component of a reflected pulsed light beam detected by the image sensor 113 is higher than the intensity of the falling component thereof, the number of times of exposure for detecting the rising component may be smaller than the number of times of exposure for detecting the falling component as illustrated in FIG. 14.

As described above, the imaging apparatus 101 in this embodiment includes the first light source 103, which emits a pulsed light beam onto the object 102, the image sensor 113, the control circuit 114, and the signal processing circuit 115. The image sensor 113 has pixels. Each of the pixels has the photodiode 403 and the floating diffusion layers 404 and 405. The first light source 103 emits a pulsed light beam having a first wavelength range (e.g., a wavelength range around 750 nm). The control circuit 114 controls a timing when a pulsed light beam is emitted by the first light source 103, a timing when the signal charge is accumulated in the floating diffusion layer 404, a timing when the signal charge is accumulated in the floating diffusion layer 405, and a timing when the signal charge is discharged. The control circuit 114 performs the following operation.

(1) In the first frame period, causing the first light source 103 to emit a pulsed light beam.

(2) In a period including at least part of the rising period that is a period when the surface reflection component I1 of a pulsed light beam emitted by the first light source 103 enters the image sensor 113 after being reflected mainly from the surface of the object 102, accumulating the signal charge in the floating diffusion layer 404 by causing the image sensor 113 to be a state where the signal charge is accumulated in the floating diffusion layer 404 and to be a state where the signal charge is not discharged. Then, after the rear end of the surface reflection component I1 of a pulsed light beam emitted by the first light source 103 enters the image sensor 113, in a period when the internal dispersion component I2 is returned to enter the image sensor 113 after being dispersed in the object 102, accumulating the signal charge in the floating diffusion layer 405 by causing the image sensor 113 to be a state where the signal charge is accumulated in the floating diffusion layer 405 and to be a state where the signal charge is not discharged.

(3) Repeating the operation of (2) within one frame.

(4) The signal processing circuit 115 calculates an amount of change in a blood flow in the rising component based on the signal accumulated in the floating diffusion layer 404 and calculates an amount of change in a blood flow in the falling component based on the signal accumulated in the floating diffusion layer 405. Thereafter, the signal processing circuit 115 obtains a distribution of an amount of change in blood flow of a skin blood flow and a cerebral blood flow.

This embodiment is described using light having one wavelength; however, the number of the floating diffusion layers may be increased in accordance with increase of the number of light having wavelengths different from each other. Increase of the number of light having wavelengths different from each other that is emitted on the object 102 makes it possible to obtain a change in concentration of hemoglobin in blood.

According to the above configuration and operation, detecting the rising component and the falling component of each of pulsed light beams having different wavelengths reflected from a living body within each frame makes it possible to quickly obtain a distribution of a change in blood flow of a skin blood flow and a cerebral blood flow. This allows a frame rate in this embodiment to be faster than that in Embodiments 1 to 3.

What is claimed is:

1. An imaging apparatus, comprising:
    a light source that emits a light pulse onto an object; and
    a light detector that detects a reflected light pulse returning from the object, wherein:
    the light detector detects a first part of the reflected light pulse in a first period,
    the light detector detects a second part of the reflected light pulse in a second period,
    the first period includes at least a part of a rising period, the rising period being a period from start to end of increase of intensity of the reflected light pulse, and
    the second period includes a part of a falling period and starts after start of the falling period, the falling period being a period from start to end of decrease of the intensity.

2. The imaging apparatus according to claim 1, wherein the light detector is an image sensor that includes pixels, each of the pixels including:
    a photoelectric converter that converts light returning from the object into signal charges, and
    an accumulator that accumulates the signal charges, and
    the image sensor accumulates the signal charges by the accumulator in the first period and accumulates the signal charges by the accumulator in the second period.

3. The imaging apparatus according to claim 2, wherein the image sensor does not accumulate the signal charges by the accumulator in a third period that is between the rising period and the falling period.

4. The imaging apparatus according to claim 2, wherein in each of frame periods, the image sensor acquires an image of the object of one frame based on the signal charges accumulated in the accumulator,
    the frame periods include a first frame period and a second frame period that is different from the first frame period, and
    the first period and the second period are included in the first frame period and the second frame period respectively.

5. The imaging apparatus according to claim 2, wherein each of the pixels includes a first accumulator and a second accumulator, and
    the image sensor accumulates the signal charges by the first accumulator in the first period and accumulates the signal charges by the second accumulator in the second period.

6. The imaging apparatus according to claim 5, wherein in each of frame periods, the image sensor acquires an image of the object of one frame based on the signal charges accumulated in the first accumulator and the second accumulator, and
    the first period and the second period are included in the same frame period in the frame periods.

7. The imaging apparatus according to claim 1, wherein the first period and the second period are discontinuous.

8. The imaging apparatus according to claim 1, wherein the first period and the second period are shorter than a pulse width of the light pulse.

9. The imaging apparatus according to claim 2, wherein the light source emits a first light pulse and a second light pulse onto the object, each of the first light pulse and the second light pulse being the light pulse, the light detector detects a first reflected light pulse and a second reflected light pulse returning from the object, each of the first reflected light pulse and the second reflected light pulse being the reflected light pulse, and the image sensor accumulates the signal charges by the accumulator in the first period of the first reflected light pulse and accumulates the signal charges by the accumulator in the second period of the second reflected light pulse.

10. The imaging apparatus according to claim 2, wherein the light source emits a plurality of light pulses onto the object, each of the plurality of light pulses being the light pulse, the light detector detects a plurality of reflected light pulses returning from the object, each of the plurality of reflected light pulses being the reflected light pulse, the image sensor accumulates the signal charges by the accumulator in first periods and accumulates the signal charges by the accumulator in second periods, each of the first periods is the first period while each of the second periods is the second period, and the number of the first periods is smaller than the number of the second periods.

11. The imaging apparatus according to claim 1, wherein the light detector does not detect the reflected light pulse in a third period that is between the rising period and the falling period.

12. An imaging apparatus, comprising:
a light source that emits a first light pulse and a second light pulse onto an object; and
a light detector that detects a first reflected light pulse returning from the object in a first period of the first reflected light pulse and a second reflected light pulse returning from the object in a second period of the second reflected light pulse, wherein:
the first period includes at least a part of a rising period, the rising period being a period from start to end of increase of intensity of the first reflected light pulse, and
the second period includes a part of a falling period and starts after start of the falling period, the falling period being a period from start to end of decrease of intensity of the second reflected light pulse.

13. The imaging apparatus according to claim 12, wherein the light detector is an image sensor that includes pixels, each of the pixels including:
a photoelectric converter that converts light returning from the object into signal charges, and
an accumulator that accumulates the signal charges, and the image sensor accumulates the signal charges by the accumulator in the first period and accumulates the signal charges by the accumulator in the second period.

14. The imaging apparatus according to claim 13, wherein in each of frame periods, the image sensor acquires an image of the object of one frame based on the signal charges accumulated in the accumulator, the frame periods include a first frame period and a second frame period that is different from the first frame period, and the first period and the second period are included in the first frame period and the second frame period respectively.

15. The imaging apparatus according to claim 13, wherein each of the pixels includes a first accumulator and a second accumulator, and the image sensor accumulates the signal charges by the first accumulator in the first period and accumulates the signal charges by the second accumulator in the second period.

16. The imaging apparatus according to claim 15, wherein in each of frame periods, the image sensor acquires an image of the object of one frame based on the signal charges accumulated in the first accumulator and the second accumulator, and the first period and the second period are included in the same frame period in the frame periods.

17. The imaging apparatus according to claim 12, wherein the first period and the second period are discontinuous.

18. The imaging apparatus according to claim 12, wherein the first period is shorter than a pulse width of the first light pulse.

19. The imaging apparatus according to claim 12, wherein the second period is shorter than a pulse width of the second light pulse.

20. The imaging apparatus according to claim 13, wherein the light source emits a plurality of light pulses including the first light pulse and the second light pulse onto the object, the light detector detects a plurality of reflected light pulses including the first reflected light pulse and the second reflected light pulse, the image sensor accumulates the signal charges by the accumulator in first periods and accumulates the signal charges by the accumulator in second periods, each of the first periods is the first period while each of the second periods is the second period, and the number of the first periods is smaller than the number of the second periods.

* * * * *